United States Patent
Conway et al.

(10) Patent No.: US 11,690,921 B2
(45) Date of Patent: Jul. 4, 2023

(54) DELIVERY OF TARGET SPECIFIC NUCLEASES

(71) Applicants: Sangamo Therapeutics, Inc., Richmond, CA (US); Life Technologies Corporation, Carlsbad, CA (US)

(72) Inventors: Anthony Conway, Richmond, CA (US); Xavier de Mollerat du Jeu, Encinitas, CA (US); Shikha Mishra, San Diego, CA (US)

(73) Assignees: Sangamo Therapeutics, Inc., Brisbane, CA (US); Life Technologies Corporation, Carlsbad, CA (US)

(*) Notice: Subject to any disclaimer, the term of this patent is extended or adjusted under 35 U.S.C. 154(b) by 1060 days.

(21) Appl. No.: 16/413,144

(22) Filed: May 15, 2019

(65) Prior Publication Data

US 2019/0365924 A1 Dec. 5, 2019

Related U.S. Application Data

(60) Provisional application No. 62/673,279, filed on May 18, 2018.

(51) Int. Cl.
| | |
|---|---|
| *A61K 48/00* | (2006.01) |
| *C12N 15/88* | (2006.01) |
| *C12N 15/113* | (2010.01) |
| *C12N 9/22* | (2006.01) |
| *A61K 9/51* | (2006.01) |
| *C07K 14/47* | (2006.01) |
| *A61P 11/00* | (2006.01) |
| *A61K 38/00* | (2006.01) |

(52) U.S. Cl.
CPC ........ *A61K 48/0033* (2013.01); *A61K 9/5123* (2013.01); *A61P 11/00* (2018.01); *C07K 14/4712* (2013.01); *C12N 9/22* (2013.01); *C12N 15/113* (2013.01); *C12N 15/88* (2013.01); *A61K 38/00* (2013.01); *C12N 2320/32* (2013.01); *C12N 2800/80* (2013.01)

(58) Field of Classification Search
CPC .. A61K 35/76; A61K 48/0008; A61K 9/1271; A61K 9/5123; C12N 15/11; C12N 15/88; C12N 15/907; C12N 2310/20; C12N 2800/80; C12N 9/22
USPC ................................................ 424/450, 93.21
See application file for complete search history.

(56) References Cited

U.S. PATENT DOCUMENTS

| | | |
|---|---|---|
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,689,558 B2 | 2/2004 | Case |
| 6,794,136 B1 | 9/2004 | Eisenberg et al. |
| 6,824,978 B1 | 11/2004 | Cox, III et al. |
| 6,833,252 B1 | 12/2004 | Dujon et al. |
| 6,903,185 B2 | 6/2005 | Kim et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,074,596 B2 | 7/2006 | Darzynkiewicz et al. |
| 7,153,949 B2 | 12/2006 | Kim et al. |
| 7,163,824 B2 | 1/2007 | Cox, III et al. |
| 7,166,745 B1 | 1/2007 | Chu et al. |
| 7,173,154 B2 | 2/2007 | Chu et al. |
| 7,253,273 B2 | 8/2007 | Collingwood |
| 7,262,054 B2 | 8/2007 | Jamieson et al. |
| 7,323,594 B2 | 1/2008 | Chu et al. |
| 7,361,635 B2 | 4/2008 | Miller et al. |
| 7,470,817 B2 | 12/2008 | Chu et al. |
| 7,479,573 B2 | 1/2009 | Chu et al. |
| 7,601,872 B2 | 10/2009 | Chu et al. |
| 7,888,121 B2 | 2/2011 | Urnov et al. |
| 7,914,796 B2 | 3/2011 | Miller et al. |
| 7,915,450 B2 | 3/2011 | Chu et al. |
| 7,951,925 B2 | 5/2011 | Ando et al. |
| 7,972,854 B2 | 7/2011 | Miller et al. |
| 8,034,598 B2 | 10/2011 | Miller |
| 8,110,379 B2 | 2/2012 | DeKelver et al. |
| 8,153,773 B2 | 4/2012 | Jemielity et al. |
| 8,158,827 B2 | 4/2012 | Chu et al. |
| 8,329,986 B2 | 12/2012 | Butler et al. |
| 8,399,218 B2 | 3/2013 | Gupta et al. |
| 8,409,861 B2 | 4/2013 | Guschin et al. |
| 8,563,314 B2 | 10/2013 | Gregory et al. |
| 8,586,526 B2 | 11/2013 | Gregory et al. |
| 8,597,912 B2 | 12/2013 | Collingwood et al. |

(Continued)

FOREIGN PATENT DOCUMENTS

| | | |
|---|---|---|
| GB | 2338237 A | 12/1999 |
| WO | WO 95/19431 A1 | 7/1995 |

(Continued)

OTHER PUBLICATIONS

Albelda, et al., "Gene Therapy for Lung Disease: Hype or Hope?" *Ann Intern Med* 132(8):649-660 (2000).

(Continued)

*Primary Examiner* — Janet L Epps-Smith
(74) *Attorney, Agent, or Firm* — Foley & Lardner LLP

(57) ABSTRACT

Described herein are lipid nanoparticles comprising cationic lipids and other lipids and also comprising engineered nucleases facilitate transfer of nucleic acids to cells.

24 Claims, 2 Drawing Sheets

Specification includes a Sequence Listing.

(56) References Cited

U.S. PATENT DOCUMENTS

| | | |
|---|---|---|
| 8,623,618 B2 | 1/2014 | Doyon et al. |
| 8,697,359 B1 | 4/2014 | Zhang |
| 8,703,489 B2 | 4/2014 | Wang |
| 8,771,985 B2 | 7/2014 | Cui et al. |
| 8,772,453 B2 | 7/2014 | Paschon et al. |
| 8,785,200 B2 | 7/2014 | Chu et al. |
| 8,871,905 B2 | 10/2014 | Holmes et al. |
| 8,895,264 B2 | 11/2014 | Cost et al. |
| 8,936,936 B2 | 1/2015 | Holmes et al. |
| 8,945,868 B2 | 2/2015 | Collingwood et al. |
| 8,956,828 B2 | 2/2015 | Bonini et al. |
| 8,962,281 B2 | 2/2015 | Doyon et al. |
| 9,005,973 B2 | 4/2015 | Cost et al. |
| 9,045,763 B2 | 6/2015 | DeKelver et al. |
| 9,150,847 B2 | 10/2015 | Rebar |
| 9,161,995 B2 | 10/2015 | Guschin et al. |
| 9,200,266 B2 | 12/2015 | Wang |
| 9,206,404 B2 | 12/2015 | Cui et al. |
| 9,222,105 B2 | 12/2015 | Cost et al. |
| 9,255,250 B2 | 2/2016 | Gregory et al. |
| 9,358,300 B2 | 6/2016 | Chu et al. |
| 9,394,545 B2 | 7/2016 | Rebar |
| 9,458,205 B2 | 10/2016 | Gregory et al. |
| 9,567,573 B2 | 2/2017 | Gregory et al. |
| 9,597,357 B2 | 3/2017 | Gregory et al. |
| 9,616,090 B2 | 4/2017 | Conway et al. |
| 9,816,074 B2 | 11/2017 | Conway et al. |
| 9,873,894 B2 | 1/2018 | Conway et al. |
| 9,877,988 B2 | 1/2018 | Rebar |
| 10,143,760 B2 | 12/2018 | Riley et al. |
| 10,179,918 B2 | 1/2019 | Cost |
| 2003/0232410 A1 | 12/2003 | Liljedahl et al. |
| 2004/0002092 A1 | 1/2004 | Arnould et al. |
| 2004/0142025 A1 | 7/2004 | MacLachlan et al. |
| 2005/0026157 A1 | 2/2005 | Baltimore et al. |
| 2005/0064474 A1 | 3/2005 | Umov et al. |
| 2005/0208489 A1 | 9/2005 | Carroll et al. |
| 2005/0267061 A1 | 12/2005 | Martin |
| 2006/0063231 A1 | 3/2006 | Li et al. |
| 2006/0078552 A1 | 4/2006 | Arnould et al. |
| 2006/0153826 A1 | 7/2006 | Arnould et al. |
| 2006/0188987 A1 | 8/2006 | Guschin et al. |
| 2006/0206949 A1 | 9/2006 | Arnould et al. |
| 2007/0042031 A1 | 2/2007 | MacLachan et al. |
| 2007/0117128 A1 | 5/2007 | Smith et al. |
| 2007/0218528 A1 | 9/2007 | Miller |
| 2008/0131962 A1 | 6/2008 | Miller |
| 2008/0159996 A1 | 7/2008 | Ando et al. |
| 2009/0068164 A1 | 3/2009 | Segal et al. |
| 2009/0136465 A1 | 5/2009 | Merenick et al. |
| 2009/0305346 A1 | 12/2009 | Miller |
| 2010/0218264 A1 | 8/2010 | Cui et al. |
| 2011/0201055 A1 | 8/2011 | Doyon et al. |
| 2011/0265198 A1 | 10/2011 | Gregory et al. |
| 2012/0017290 A1 | 1/2012 | Cui et al. |
| 2012/0040398 A1 | 2/2012 | Miller |
| 2012/0060230 A1 | 3/2012 | Collingwood et al. |
| 2012/0195936 A1 | 8/2012 | Rudolph et al. |
| 2013/0122591 A1 | 5/2013 | Cost et al. |
| 2013/0137104 A1 | 5/2013 | Cost et al. |
| 2013/0177960 A1 | 7/2013 | Rebar |
| 2013/0177983 A1 | 7/2013 | Rebar |
| 2014/0017212 A1 | 1/2014 | Rebar |
| 2015/0056705 A1 | 2/2015 | Conway et al. |
| 2015/0159172 A1 | 6/2015 | Miller et al. |
| 2015/0335708 A1 | 11/2015 | Froelich et al. |
| 2017/0107539 A1 | 4/2017 | Yu et al. |
| 2017/0173080 A1 | 6/2017 | Lee et al. |
| 2018/0087072 A1 | 3/2018 | Miller et al. |
| 2019/0060482 A1* | 2/2019 | Mishra ............ A61K 47/6917 |

FOREIGN PATENT DOCUMENTS

| | | | |
|---|---|---|---|
| WO | WO 96/06166 A1 | 2/1996 | |
| WO | WO 98/37186 A1 | 8/1998 | |
| WO | WO 98/53057 A1 | 11/1998 | |
| WO | WO 98/53058 A1 | 11/1998 | |
| WO | WO 98/53059 A1 | 11/1998 | |
| WO | WO 98/53060 A1 | 11/1998 | |
| WO | WO 98/54311 A1 | 12/1998 | |
| WO | WO 00/27878 A1 | 5/2000 | |
| WO | WO 01/60970 A2 | 8/2001 | |
| WO | WO 01/88197 A2 | 11/2001 | |
| WO | WO 02/16536 A1 | 2/2002 | |
| WO | WO 02/099084 A2 | 12/2002 | |
| WO | WO 03/016496 A2 | 2/2003 | |
| WO | WO 2007/014275 A2 | 2/2007 | |
| WO | WO-2009146179 A1 * | 12/2009 | ......... C07K 14/4702 |
| WO | WO 2010/079430 A1 | 7/2010 | |
| WO | WO 2013/016058 A1 | 1/2013 | |
| WO | WO 2013/086373 A1 | 6/2013 | |
| WO | WO 2015/199952 A1 | 12/2015 | |
| WO | WO 2016/011203 A1 | 1/2016 | |
| WO | WO 2016/183298 A2 | 11/2016 | |
| WO | WO 2017/004143 A1 | 1/2017 | |
| WO | WO 2017/075531 A1 | 5/2017 | |
| WO | WO-2017072590 A1 * | 5/2017 | ........... A61K 38/465 |
| WO | WO 2018/204469 A2 | 11/2018 | |
| WO | WO-2018204469 A2 * | 11/2018 | ............. A61K 35/42 |

OTHER PUBLICATIONS

Amreddy, et al., "Polymeric Nanoparticle-Mediated Gene Delivery for Lung Cancer Treatment," *Top Curr Chem (Cham)* 375(2):35 (2017).

Argast, et al., "I-PPOL and I-CREI Homing Site Sequence Degneracy Determined by Random Mutagenesis and Sequential in Vitro Enrichment," *J. Mol. Biol.* 280:345-353 (1998).

Ashworth, et al., "Computational Redesign of Endonuclease DNA Binding and Cleavage Specificity," *Nature* 441(7093):656-659 (2006).

Beerli, et al., "Engineering Polydactyl Zinc-Finger Transcription Factors," *Nature Biotechnology* 20:135-141 (2002).

Belfort, et al., "Homing Endonucleases: Keeping the House in Order," *Nucleic Acids Res.* 25(17):3379-3388 (1997).

Beurdeley, et al., "Compact Designer Talens for Efficient Genome Engineering," *Nat Comm* 4(1762):1-8. doi: 10.1038/ncomms2782 (2013).

Boch, et al., "Breaking the Code of DNA Binding Specificity of TAL-Type III Effectors," *Science* 326:1509-1512 (2009).

Boissel, et al., "Megatals: A Rare-Cleaving Nuclease Architecture for Therapeutic Genome Engineering," *Nucleic Acids Research* 42(4):2591-2601. doi:10.1093/nar/gktl224 (2013).

Bonas, et al., "Genetic and Structural Characterization of the Avirulence Gene AVRBS3 From *Xanthomonas campestris* Pv. Vesicatoria," *Mol Gen Genet* 218:127-136 (1989).

Burstein, et al., "New CRISPR-CAS Systems From Uncultivated Microbes," *Nature* 542(7640):237-241 (2017).

Cebrian-Serrano, et al., "CRISPR-CAS Orthologues and Variants: Optimizing the Repertoire, Specificity and Delivery of Genome Engineering Tools," *Mamm Genome* 28(7):247-261 (2017).

Chevalier, et al., "Design, Activity, and Structure of a Highly Specific Ariificial Endonuclease," *Molecular Cell* 10:895-905 (2002).

Chilton, et al., "Targeted Integration of T-DNA Into the Tobacco Genome at Double-Stranded Breaks: New Insights on the Mechanism of T-DNA Integration," *Plant Physiology.* 133(3):956-65 (2003).

Choo, et al., "Advances in Zinc Finger Engineering," *Current Opinion in Structural Biology* 10:411-416 (2000).

Dujon, et al., "Mobile Introns: Definition of Terms and Recommended Nomenclaure," *Gene* 82(1):115-118 (1989).

Elborn, "Cystic Fibrosis," *The Lancet* 388(10059):2519-2531 (2016).

Epinat, et al., "A Novel Engineered Meganuclease Induces Homologous Recombination in Yeast and Mammalian Cells," *Nucleic Acids Res.* 31(11):2952-2962 (2003).

Fagerlund, et al., "The CPF1 CRISPR-CAS Protein Expands Genome-Editing Tools," *Genom Bio* 16:251 (2015).

Gimble, et al., "Substrate Recognition and Induced DNA Distortion by the PI-SCEL Endonuclease, an Enzyme Generated by Protein Splicing," *J. Mol. Biol.* 263(2):163-180 (1996).

(56) References Cited

OTHER PUBLICATIONS

Gouble, et al., "Efficient In Toto Targeted Recombination in Mouse Liver by Meganuclease-Induced Double-Strand Break," *J. Gene Med.* 8(5):616-622 (2006).
Guillinger, et al., "Fusion of Catalytically Inactive CAS9 to FOKL Nuclease Improves the Specificity of Genome Modification," *Nature Biotech.* 32(6):577-582 (2014).
Guo, et al., "Directed Evolution of an Enhanced and Highly Efficient FOKI Cleavage Domain for Zinc Finger Nucleases," *J. Mol. Biol.* 400(1):96-107 doi.10.1016/j.jmb.2010.04.060 (2010).
Hafez, et al., "On the Mechanism Whereby Cationic Lipids Promote Intracellular Delivery of Polynucleic Acids," *Gene Ther* 8(15):1188-1196 (2001).
Haft, et al., "A Guild Of 45 CRISPR-Associated (CAS) Protein Families and Multiple CRISPR/CAS Subtypes Exist in Prokaryotic Genomes," *PLoS Computational Biology* 1(6)e60:474-483 (2005).
Heuer, et al., "Repeat Domain Diversity of AVRBS3-LIKE Genes in Ralstonia Solanacearum Strains and Association With Host Preferences in the Field," *Applied and Environmental Microbiology* 73(13):4379-4384 (2007).
Isalan, et al., "A Rapid, Generally Applicable Method to Engineer Zinc Fingers Illustrated by Targeting the HIV-1 Promoter," *Nat Biotechnol.* 19(7):656-660 (2001).
Jansen, et al., "Identification of Genes That Are Associated With DNA Repeats in Prokaryotes," *Molecular Microbiology* 43(6):1565-1575 (2002).
Jasin, "Genetic Manipulation of Genomes With Rare-Cutting Endonucleases," *Trends Genet.* 12(6):224-228 (1996).
Kariko, et al., "Generating the Optimal MRNA for Therapy: HPLC Purification Eliminates Immune Activation and Improves Translation of Nucleoside-Modified, Protein-Encoding MRNA," *Nucleic Acid Research* 39(21):e142. doi.10.1093/nar/gkr695 (2011).
Kay, et al., "A Bacterial Effector Acts as a Plant Transcription Factor and Induces a Cell Size Regulator," *Science* 318:648-651 (2007).
Kim, et al., "Hybrid Restriction Enzymes: Zinc Finger Fusions to FOK I Cleavage Domain," *Proc Nat'l Acad Sci USA* 93(3):1156-1160 (1996).
Kleinstiver, et al., "High-Fidelity CRISPR-CAS9 Variants With Undetectable Genome-Wide Off-Targets," *Nature* 529(7587):490-495. doi: 10.1038/nature16526 (2016).
Kormann, et al., "Expression of Therapeutic Proteins After Delivery of Chemically Modified MRNA in Mice," *Nature Biotechnology* 29(2):154-157 (2011).
Laube, "Aerosolized Medications for Gene and Peptide Therapy," *Respiratory Care* 60(6):806-824 (2015).
Lee, et al., "Nanoparticle-Based Targeted Gene Therapy for Lung Cancer," *Am J Cancer Res* 6(5):1118-1134 (2016).
Li, et al., "Transepithelial Electrical Measurements With the Ussing Chamber," *J. Cystic Fibrosis* 3(Suppl. 2):123-126 (2004).
Ma, et al., "Rational Design of MINI-CAS9 for Transcriptional Activation," *ACS Synth Biol* 7(4):978-985 (2018).
Makarova, et al., "A DNA Repair System Specific for Thermophilic Archaea and Bacteria Predicted by Genomic Context Anlysis," *Nucleic Acids Research* 30(2):482-496 (2002).
Makarova, et al., "A Putative RNA-Interference-Based Immune System in Prokaryotes: Computational Analysis of the Predicted Enzymatic Machinery, Functional Analogies With Eukaryotic RNAI, and Hypothetical Mechanisms of Action," *Biology Direct* 1(7):1-26 (2006).
McCaffery, et al., "CRISPR-CAS9 D10A Nickase Target-Specific Fluorescent Labeling of Double Strand DNA for Whole Genome Mapping and Structural Variation Analysis," *Nucleic Acids Res.* 44(2):e11 doi:10.1093/nar/gkv878. (2016).
Miller, et al., "An Improved Zinc-Fingernuclease Architecture for Highly Specific Genome Editing," *Nat Biotechnol* 25(7):778-784 (2007).
Monnat, Jr., et al., "Generation of Highly Site-Specific DNA Doublestrand Breaks in Human Cells by the Homing Endonucleases I-PPOI and I-CREI," *Biochem. Biophysics. Res. Common.* 255(1):88-93 (1999).
Moscou, et al., "A Simple Cipher Governs DNA Recognition by TAL Effectors," *Science* 326:1501 (2009).
Mottais, et al., "Enhancement of Lung Gene Delivery After Aerosol: A New Strategy Using Non-Viral Complexes With Antibacterial Properties," *Bioscience Reports* 37(6):BSR20160618 (2017).
Olovnikov, et al., "Bacterial Argonaute Samples the Transcriptome to Identify Foreign DNA," *Molecular Cell* 51:594-605 (2013).
Pabo, et al., "Design and Selection of Novel CYS2-HIS2 Zinc Finger Proteins," *Ann. Rev. Biochem.* 70:313-340 (2001).
Pâques, et al., "Meganucleases and DNA Double-Strand Break-Induced Recombination: Perspectives for Gene Therapy," *Current Gene Therapy* 7(1):49-66 (2007).
Perez, et al., "Establishment of HIV-1 Resistance in CD4+ T Cells by Genome Editing Using Zinc-Finger Nucleases," *Nature Biotechnology* 26(7):808-816 (2008).
Perler, et al., "Protein Splicing Elements: Inteins and Exteins—A Definition of Terms and Recommended Nomenclature," *Nucleic Acids Res.* 22(7):1125-1127 (1994).
Porteus, et al., "Gene Targeting Using Zinc Finger Nucleases," *Nat. Biotechnol.* 23(8):967-73 (2005).
Puchta, et al., "Two Different but Related Mechanisms are Used in Plants for the Repair of Genomic Double-Strand Breaks by Homologous Recombination," *Proc. Natl. Acad. Sci. USA* 93(10):5055-60 (1996).
Ran, et al., "In Vivo Genome Editing Using *Staphylococcus aureus* CAS9," *Nature* 520:186 (2015).
Roberts, et al., "Rebase: Restriction Enzymes and Methyltransferases," *Nucleic Acids Res.* 31(1):418-420 (2003).
Rong, et al., "Targeted Mutagenesis by Homologous Recombination in *D. melanogaster*," *Genes Dev.* 16(12):1568-81 (2002).
Route, et al., "Introduction of Double-Strand Breaks Into the Genome of Mouse Cells by Expression of a Rare-Cutting Endonuclease," *Mol. Cell. Biol.* 14(12):8096-106 (1994).
Russell, et al., "The Stability of Human Beta-Globin MRNA is Dependent on Struciural Determinants Positioned Within Its 3' Untranslated Region," *Blood* 87(12):5314-5323 (1996).
Schomack, et al., "Gene-For-Gene-Mediated Recognition of Nuclear-Targeted AVRBS3-Like Bacterial Effector Proteins," *Journal of Plant Physiology* 163(3):256-272 (2006).
Segal, et al., "Custom DNA-Binding Proteins Come of Age: Polydactyl Zinc-Finger Proteins," *Current Opinion Biotechnology* 12:632-637(2001).
Semple, et al., "Interactions of Liposomes and Lipid-Based Carrier Systems With Blood Proteins: Relation to Clearance Behaviour In Vivo," *Adv. Drug Deliv Rev* 32(1-2):3-17 (1998).
Sheng, et al., "Structure-Based Cleavage Mechanism of Thermus Thermophilus Argonaute DNA Guide Strand-Mediated DNA Target Cleavage," *Proc. Natl. Acad. Sci. U.S.A.* 111(2):652-657 (2014).
Smietanski, et al., "Structural Analysis of Human 2'-0-Ribose Methyltransferases Involved in MRNA Cap Structure Formation," *Nature Communications* 5:3004 (2014).
Sussman, et al., "Isolation and Characterization of New Homing Endonuclease Specificities at Individual Target Site Positions," *J. Mol. Biol.* 342(1):31-41 (2004).
Swarts, et al., "DNA-Guided DNA Interference by a Prokaryotic Argonau IE," *Nature* 507(7491):258-261 (2014).
Troung, et al., "Development of an Intein-Mediated SPLIT-CAS9 System for Gene Therapy," *Nucl Acid Res* 43(13):6450-8 (2015).
Umov, et al., "Highly Efficient Endogenous Human Gene Correction Using Designed Zinc-Fingernucleases," *Nature* 435(7042):646-651 (2005).
Vogel, "A Bacterial Seek-And-Destroy System for Foreign DNA," *Science* 344(6187):972-973 (2014).
Yin, et al., "Therapeutic Genome Editing by Combined Viral and Non-Viral Delivery of CRISPR System Components In Vivo," *Nat Biotechnol* (2016).
Yuan, et al., "Crystal Structure of A. Aeolicus Argonaute, a Sitespecific DNA-Guided Endoribonuclease, Provides Insights Into Risc-Mediated mRNA Cleavage," *Molecular Cell* 19:405-419 (2005).
Zanta-Boussif, et al., "Validation of a Mutated Pre Sequence Allowing High and Sustained Transgene Expression While Abrogating WHV-X Protein Synthesis: Application To the Gene Therapy of Was," *Gene Ther* 16(5):605-19 (2009).

(56) References Cited

OTHER PUBLICATIONS

Zetsche, et al., "A Split-CAS9 Architecture for Inducible Genome Editing and Transcription Modulation," *Nat Biotechnol* 33(2):139-142 (2015).

* cited by examiner

SEQUENCE LISTING

```
<160> NUMBER OF SEQ ID NOS: 29

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Gly Glu Lys Pro
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Gly Gly Gln Arg Pro
1               5

<210> SEQ ID NO 3
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 3

Thr Gly Gln Lys Pro
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Gly Ser Gln Lys Pro
1               5

<210> SEQ ID NO 5
<211> LENGTH: 196
<212> TYPE: PRT
<213> ORGANISM: Planomicrobium okeanokoites

<400> SEQUENCE: 5

Gln Leu Val Lys Ser Glu Leu Glu Glu Lys Ser Glu Leu Arg His
1               5                   10                  15

Lys Leu Lys Tyr Val Pro His Glu Tyr Ile Glu Leu Ile Glu Ile Ala
                20                  25                  30

Arg Asn Ser Thr Gln Asp Arg Ile Leu Glu Met Lys Val Met Glu Phe
            35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
            195

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 6

Asp Arg Ser His Leu Thr Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Ser Gly Asp Leu Thr Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Arg Ser Asn Arg Thr Thr
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Ser Asp Ala Leu Ala Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ser Asp Asn Leu Ser Glu
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Arg Ala Asn Arg Asn Ser
1               5
```

```
<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Arg Ser Ala Leu Ser Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Thr Ser Gly Ser Leu Thr Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Ser Ser Asp Leu Ser Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Trp Arg Lys Ser Leu Lys Val
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Leu Asp Trp Leu Pro Met
1               5

<210> SEQ ID NO 17
<211> LENGTH: 28
<212> TYPE: DNA
<213> ORGANISM: Mus sp.

<400> SEQUENCE: 17
gtcaacaggt gtactgcagg catgctag                                     28
```

```
<210> SEQ ID NO 18
<211> LENGTH: 28
<212> TYPE: DNA
<213> ORGANISM: Mus sp.

<400> SEQUENCE: 18
ccctgggtta tgctgtgatc ttgtgtca                                              28

<210> SEQ ID NO 19
<211> LENGTH: 51
<212> TYPE: DNA
<213> ORGANISM: Xenopus sp.

<400> SEQUENCE: 19
tgcttgttct ttttgcagaa gctcagaata aacgctcaac tttggcagat c                    51

<210> SEQ ID NO 20
<211> LENGTH: 284
<212> TYPE: DNA
<213> ORGANISM: Unknown
<220> FEATURE:
<223> OTHER INFORMATION: Description of Unknown:
      HBB 3' UTR sequence

<400> SEQUENCE: 20
ctagaagctc gctttcttgc tgtccaattt ctattaaagg ttcctttgtt ccctaagtcc           60
aactactaaa ctgggggata ttatgaaggg ccttgagcat ctggattctg cctaataaaa         120
aacatttatt ttcattgctg cgctagaagc tcgctttctt gctgtccaat ttctattaaa         180
ggttcctttg ttccctaagt ccaactacta aactggggga tattatgaag ggccttgagc         240
atctggattc tgcctaataa aaaacattta ttttcattgc tgcg                           284

<210> SEQ ID NO 21
<211> LENGTH: 592
<212> TYPE: DNA
<213> ORGANISM: Woodchuck hepatitis virus

<400> SEQUENCE: 21
aatcaacctc tggattacaa aatttgtgaa agattgactg gtattcttaa ctatgttgct          60
ccttttacgc tatgtggata cgctgcttta atgcctttgt atcatgctat tgcttcccgt        120
atggctttca ttttctcctc cttgtataaa tcctggttgc tgtctcttta tgaggagttg        180
tggcccgttg tcaggcaacg tggcgtggtg tgcactgtgt ttgctgacgc aacccccact        240
ggttggggca ttgccaccac ctgtcagctc ctttccggga ctttcgcttt ccccctccct        300
attgccacgg cggaactcat cgccgcctgc cttgcccgct gctggacagg ggctcggctg        360
ttgggcactg acaattccgt ggtgttgtcg gggaagctga cgtcctttcc atggctgctc        420
gcctgtgttg ccacctggat tctgcgcggg acgtccttct gctacgtccc ttcggccctc        480
aatccagcgg accttccttc ccgcggcctg ctgccggctc tgcggcctct tccgcgtctt        540
cgccttcgcc ctcagacgag tcggatctcc ctttgggccg cctccccgcc tg                592

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 22

Leu Arg Gly Ser Gln Leu Val Lys Ser
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Gly Ala Gln Ser Thr Leu Asp Phe
1               5

<210> SEQ ID NO 24
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
aaaaaaaaaa aaaaaaaaaa aaaaaaaaaa aaaaaaaaaa aaaaaaaaaa           50

<210> SEQ ID NO 25
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
aaaaaaaaaa aaaaaaaaaa aaaaaaaaaa aaaaaaaaaa aaaaaaaaaa a         51

<210> SEQ ID NO 26
<211> LENGTH: 64
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
aaaaaaaaaa aaaaaaaaaa aaaaaaaaaa aaaaaaaaaa aaaaaaaaaa aaaaaaaaaa  60
aaaa                                                              64

<210> SEQ ID NO 27
<211> LENGTH: 128
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 27
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120
aaaaaaaa                                                          128

```
<210> SEQ ID NO 28
<211> LENGTH: 193
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 28
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaa                                                        193

<210> SEQ ID NO 29
<211> LENGTH: 9
<212> TYPE: PRT
<213> ORGANISM: Unknown
<220> FEATURE:
<223> OTHER INFORMATION: Description of Unknown:
      "LAGLIDADG" family peptide motif sequence

<400> SEQUENCE: 29

Leu Ala Gly Leu Ile Asp Ala Asp Gly
1               5
```

DELIVERY OF TARGET SPECIFIC NUCLEASES

CROSS-REFERENCE TO RELATED APPLICATIONS

The present application claims the benefit of U.S. Provisional Application No. 62/673,279, filed May 18, 2018, the disclosure of which is hereby incorporated by reference in its entirety.

SEQUENCE LISTING

The instant application contains a Sequence Listing which has been filed electronically in ASCII format and is hereby incorporated by reference in its entirety. Said ASCII copy, created on Jul. 15, 2019, is named 8325-0174_SL.txt and is 9,268 bytes in size.

TECHNICAL FIELD

The present disclosure is in the fields of polypeptide and genome engineering and the use of cationic lipids and other lipid components to facilitate transfer of nucleic acids to cells.

BACKGROUND

Gene therapy holds enormous potential for a new era of human therapeutics. These methodologies will allow treatment for conditions that heretofore have not been addressable by standard medical practice. One area that is especially promising is the ability to add a transgene to a cell to cause that cell to express a product that previously was not being produced in that cell. Examples of uses of this technology include the insertion of a gene encoding a therapeutic protein, insertion of a coding sequence encoding a protein that is somehow lacking in the cell or in the individual and insertion of a sequence that encodes a structural nucleic acid such as a microRNA.

Artificial nucleases, such as engineered zinc finger nucleases (ZFN), transcription-activator like effector nucleases (TALENs), the CRISPR/Cas system with an engineered crRNA/tracr RNA ('single guide RNA'), also referred to as RNA guided nucleases, and/or nucleases based on the Argonaute system (e.g., from *T. thermophilus*, known as 'TtAgo', (Swarts et al. (2014) *Nature* 507(7491):258-261), comprise DNA binding domains (nucleotide or polypeptide) associated with or operably linked to cleavage domains, and have been used for targeted alteration of genomic sequences. For example, nucleases have been used to insert exogenous sequences, inactivate one or more endogenous genes, create organisms (e.g., crops) and cell lines with altered gene expression patterns, and the like. See, e.g., U.S. Pat. Nos. 9,873,894; 9,394,545; 9,150,847; 9,206,404; 9,222,105; 9,045,763; 9,005,973; 8,956,828; 8,936,936; 8,945,868; 8,871,905; 8,586,526; 8,563,314; 8,329,986; 8,399,218; 6,534,261; 6,599,692; 6,503,717; 6,689,558; 7,067,317; 7,262,054; 7,888,121; 7,972,854; 7,914,796; 7,951,925; 8,110,379; 8,409,861; 8,771,985; 8,895,264; U.S. Patent Publication Nos. 2003/0232410; 2005/0208489; 2005/0026157; 2005/0064474; 2006/0063231; 2011/0265198; and 2013/0177960. For instance, a pair of nucleases (e.g., zinc finger nucleases, TALENs, dCas-Fok fusions) may be used to cleave genomic sequences. Each member of the pair generally includes an engineered (non-naturally occurring) DNA-binding protein linked to one or more cleavage domains (or half-domains) of a nuclease. When the DNA-binding proteins bind to their target sites, the cleavage domains that are linked to those DNA binding proteins are positioned such that dimerization and subsequent cleavage of the genome can occur.

Transgenes can be delivered to a cell by a variety of ways, such that the transgene becomes integrated into the cell's own genome and is maintained there. In recent years, a strategy for transgene integration has been developed that uses cleavage with site-specific nucleases for targeted insertion into a chosen genomic locus (see, e.g., U.S. Pat. No. 7,888,121). Nucleases, such as zinc finger nucleases (ZFNs), transcription activator-like effector nucleases (TALENs), or nuclease systems such as the CRISPR/Cas system (utilizing an engineered guide RNA), are specific for targeted genes and can be utilized such that the transgene construct is inserted by either homology directed repair (HDR) or by end capture during non-homologous end joining (NHEJ) driven processes. See, e.g., U.S. Pat. Nos. 9,816,074; 9,616,090; 9,873,894; 9,597,357; 9,567,573; 9,458,205; 9,394,545; 9,255,250; 9,222,105; 9,200,266; 9,045,763; 9,005,973; 9,150,847; 8,956,828; 8,945,868; 8,895,264; 8,771,985; 8,703,489; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publication Nos. 2003/0232410; 2005/0208489; 2005/0026157; 2005/0064474; 2006/0063231; 2010/0218264; and 2015/0335708, the disclosures of which are incorporated by reference in their entireties.

Transgenes may be introduced and maintained in cells in a variety of ways. Following a "cDNA" approach, a transgene is introduced into a cell such that the transgene is maintained extra-chromosomally rather than via integration into the chromatin of the cell. The transgene may be maintained on a circular vector (e.g. a plasmid, or a non-integrating viral vector such as AAV or Lentivirus), where the vector can include transcriptional regulatory sequences such as promoters, enhancers, polyA signal sequences, introns, and splicing signals (U.S. Pat. No. 10,143,760). An alternate approach involves the insertion of the transgene in a highly expressed safe harbor location such as the albumin gene (see U.S. Pat. Nos. 9,394,545 and 9,150,847). This approach has been termed the In Vivo Protein Replacement Platform™ or IVPRP. Following this approach, the transgene is inserted into the safe harbor (e.g., Albumin) gene via nuclease-mediated targeted insertion where expression of the transgene is driven by the Albumin promoter. The transgene is engineered to comprise a signal sequence to aid in secretion/excretion of the protein encoded by the transgene.

"Safe harbor" loci include loci such as the AAVS1, HPRT, Albumin and CCR5 genes in human cells, and Rosa26 in murine cells. See, e.g., U.S. Pat. Nos. 9,877,988; 9,567,573; 9,394,545; 9,222,105; 9,150,847; 7,888,121; 7,972,854; 7,914,796; 7,951,925; 8,895,264; 8,771,985; 8,110,379; 8,409,861; 8,586,526; U.S. Patent Publication Nos. 2003/0232410; 2005/0208489; 2005/0026157; 2006/0063231; 2008/0159996; and 2010/0218264. Nuclease-mediated integration offers the prospect of improved transgene expression, increased safety and expressional durability, as compared to classic integration approaches that rely on random integration of the transgene, since it allows exact transgene positioning for a minimal risk of gene silencing or activation of nearby oncogenes.

Lung diseases are prominent among the disorders for which human gene therapy protocols have been approved. From a technical perspective, delivery to the lung can be accomplished by multiple approaches—through the airway, by direct transthoracic injection, or through the dual pulmonary blood supply. From a disease perspective, the genetic basis for the two most common fatal inherited lung disorders, cystic fibrosis and al-antitrypsin deficiency, is known, and current treatment regimens are supportive but not curative. Several other pulmonary disorders, such as lung cancer, mesothelioma, pulmonary vascular diseases, radiation-induced lung injury, transplantation-induced lung injury, asthma, and pulmonary inflammation, are potential targets for gene therapy (Albelda et al. (2000) *Ann Intern Med* 132:649-660).

Cystic fibrosis (CF) is the most common life-shortening inherited disorder in Caucasians, with an incidence of about 1 in 2500 births. The molecular basis of the disease, the failure of a chloride ion channel important in creating sweat, digestive enzymes and mucus. The Δ508 mutation in the Cystic Fibrosis Transmembrane Conductance Regulator (CFTR) gene occurs in >90% of patients in the U.S., creates a protein that does not fold properly and so is not transported to the cell membrane. CFTR dysfunction mainly affects epithelial cells, although there is evidence of a role in immune cells. Although often thought of as primarily a pulmonary disease, cystic fibrosis affects several body systems, although morbidity and mortality are mostly caused by bronchiectasis, small airways obstruction, and progressive respiratory impairment. Important comorbidities caused by epithelial cell dysfunction occur in the pancreas (malabsorption), liver (biliary cirrhosis), sweat glands (heat shock), and vas deferens (infertility) (Stuart (2016) *The Lancet* 388 (10059):2519-2531).

Treatments targeting the inside of epithelial cells encounter several obstacles during their transit from the upper respiratory tract to target cells. The mucus is the first barrier whose role is to purify the air breathed in by the individual by trapping the inhaled particles. The thickness of non-pathological mucus is between 5 and 10 and it is replaced every 10-20 min on an average. Due to its composition and rheology, mucus is a key barrier against efficient inhaled therapy. This filtering structure permits the passage of particles having a size of approximately 100-200 nm. In some obstructive diseases such as CF, the mucus is more viscous and the mesh is tighter. A second surface liquid called a pulmonary surfactant is also present on the inner surface of the pulmonary alveoli and facilitates respiratory movements. It is secreted by type II pneumocytes and reduces the air/liquid surface tension on the alveoli facilitating respiration and also plays a role in immune defense. It consists of 90% lipids (mostly dipalmitoylphosphatidylcholine) and 10% proteins. In newborns, usually premature infants, a deficiency in pulmonary surfactant results in respiratory distress. Similarly, in adults, frequent alterations of the pulmonary surfactant are observed. They can occur as a result of drowning and/or acute respiratory distress syndrome. An innate defense system called mucociliary clearance helps eliminate inhaled toxicants (pollutants, microbes etc.). During inhalation, the particles are trapped in the mucus. The cilia present on the surface of the respiratory epithelium beat in a synchronized manner at a frequency of 1000-1500 beats per minute. This ciliary movement moves the mucus up to the trachea. The rate of upward movement of the mucus is between 5 and 20 mm/min. Once in the trachea, the mucus will be eliminated by the digestive tract or by expectoration. As previously stated, mucociliary clearance is a route of rapid elimination for inhaled drugs. It is therefore necessary that inhaled therapeutical drugs must not remain blocked in the mucus which favors their elimination (Mottais et al. (2017) *Bioscience Reports* 37(6): BSR20160618).

Applying gene therapy to the lung via inhalation has many obstacles. Firstly, nucleic acid molecules are fragile and cannot simply be aerosolized. As stated above, once in the lung, there are many barriers to the nucleic acids penetrating the surface barrier of the lung epithelium: the mucus and surfactant barriers described. In addition to the one already mentioned, in patients with pulmonary disease, there is often bacteria present in the pulmonary layers which can degrade non-protected nucleotides. Thus, researchers have turned to both viral and non-viral vectors to deliver nucleic acids. The use of a viral delivery system can take advantage of the fact that viral particles can be delivered via aerosolization, but they are often not very efficient. For example, for the treatment of cystic fibrosis, 24 clinical trials have been carried out using aerosolized gene vectors by 2015. 9 trials were done with adenovirus where low-level gene transfer was achieved in some subjects but lung inflammation and humoral and cellular immune responses, preventing any re-administration, were observed. 6 trials were carried out with AAV2, but no clinical efficacy was observed. Finally, 9 trials were done with non-viral gene delivery but again no efficacy was observed (Laube, Beth (2015) *Respiratory Care* 60(6):806.

Thus, there remains a need to develop new methods of delivery to the lung. One such system comprises the use of nanoparticles. Nanoparticles can be solid in nature, and comprise materials including polysaccharides, lipids, proteins, biodegradable polymers, and metal oxides. Other nanoparticles are in a liquid form, and are mainly liposomes, micelles or emulsion systems composed of amphiphilic molecules or polymers. Lipid nanoparticles (LNP) are one of the most promising types of nanoparticles due to high encapsulating efficiency of nucleic acids, high stability and compatibility with biologic environments (Lee et al. (2016) *Am J Cancer Res* 6(5):1118-1134). A variety of such LNP systems are known and are disclosed in, for example, but not limited to, U.S. Pat. Nos. 7,166,745; 7,173,154; 7,323,594; 7,470.817; 7,479,573; 7,601,872; 7,915,450; 8,158,827; 8,785,200; 9,358.300, International Patent Publication No. WO 2016/011203, and U.S. Patent Publication No. 2017/0107539, all of which are hereby expressly incorporated by reference in their entirety as though fully set forth herein. Other promising nanoparticle systems include polymer-based nanoparticles which are an alternative LNP and inorganic nanoparticles, efficiently carrying nucleic acid therapeutics while being stable in vivo (Amreddy et al. (2017) *Top Curr Chem (J)* 375(2):35).

Thus, there remains a need for additional methods and compositions to deliver gene therapy reagents to biological systems, in particular to the lungs.

SUMMARY

The present disclosure provides methods and compositions to increase the efficiency of gene therapy in pulmonary tissue through the use of LNP reagents comprising gene therapy reagents. Thus, described herein are compositions comprising LNPs capable of delivering mRNAs encoding engineered transcription factors or engineered nucleases, and/or DNAs encoding engineered transcription factors, engineered nucleases and/or donor (transgenes) for use in gene therapy. The disclosure also provides methods of using these compositions for regulation of a gene of interest, targeted cleavage of cellular chromatin in a region of interest to knock out one or more genes, and/or integration of a transgene via targeted integration at a predetermined region of interest in cells. Described herein are cationic lipid nanoparticles (LNP) comprising one or more polynucleotides (e.g., mRNA) encoding one or more zinc finger protein (ZFP) transcription factors (ZFP-TFs) or one or more zinc finger nucleases (ZFNs), optionally further comprising one or more donor polynucleotides (e.g., transgenes and/or oligonucleotides for correcting mutations). Also described are compositions (e.g., pharmaceutical compositions) comprising one or more LNPs as described herein and, optionally, one or more donor polynucleotides (e.g., carried on one or more AAV vectors). In certain embodiments, the LNPs or compositions comprising the LNPs comprise one or more ZFNs that bind to and cleave an endogenous Cystic Fibrosis Transmembrane Conductance Regulator (CFTR) gene such that the donor polynucleotide (e.g., encoded a functional CFTR protein and/or a sequence that corrects a mutation such as Δ508 mutation, in the endogenous CFTR gene) is integrated into the CFTR gene. A cell (e.g., lung cell) comprising one or more LNPs or compositions as described herein is also provided. Methods of using the LNPs and compositions comprising these LNPs for modulating gene expression, integrating a donor polynucleotide into the genome of a cell, and/or treating and/or preventing a disease (e.g., CF) in a subject in need thereof are also provided.

Thus, in one aspect, described herein are novel LNPs comprising one or more cationic lipids and comprising one or more nucleic acids (e.g., a nucleic acid (DNA and/or mRNA) encoding one or more proteins such as one or more engineered transcription factors (e.g., activators or repressors), one or more engineered nucleases, one or more donors (transgenes), one or more shRNAs, etc.). Upon delivery to a cell (in vitro or in vivo) the proteins encoded by the nucleic acids exhibit increased activity in the cell and/or provide improved tolerability to the delivery process in the cell, as compared to when the nucleic acid(s) are delivered by other (nonviral or viral) delivery mechanisms. In some embodiments, a nucleic acid of the LNP comprises one or more mRNAs that encode one or more nucleases or transcription factors. In some aspects, the engineered transcription factors comprise one or more zinc finger proteins (ZFP-TF), one or more TAL-effector domain proteins (TALE-TFs), one or more CRISPR/Cas transcription factors (CRISPR-TFs). In some aspects, the nuclease(s) comprise(s) one or more zinc finger nucleases (ZFNs). In further aspects, the nuclease(s) comprise(s) a Tale Effector-like nuclease (TALEN), one or more CRISPR/Cas nuclease(s), one or more MegaTALs and/or one or more meganuclease(s). In some embodiments, a nucleic acid of the LNP comprises a donor DNA. In some aspects, the donor DNA is a plasmid, a minigene, or a linear DNA. In further aspects, the nucleic acid comprising a DNA comprising a transgene for delivery to the cell, can serve as template for targeted integration, or can be maintained extra-chromosomally.

In some embodiments, the LNPs comprise cationic lipid molecules. In some aspects, the LNPs also comprise neutral lipids, charged lipids, steroids, including cholesterols and/or their analogs, and/or polymer conjugated lipids. In some embodiments, LNP formulations particularly suited to the efficient and stable delivery of genome engineering components discussed above and which are the subject of the embodiments set forth herein, including nucleic acids such as mRNA molecules, that encode various genome engineering components are those formulations of the type set forth explicitly in U.S. Patent Publication No. 2019/0060482, and hereby explicitly incorporated by reference in its entirety as though fully set forth herein. In certain embodiments, the LNP comprises:

(i) a first cationic lipid at a compositional molar ratio from about 0.18 to about 0.32 and of formula:

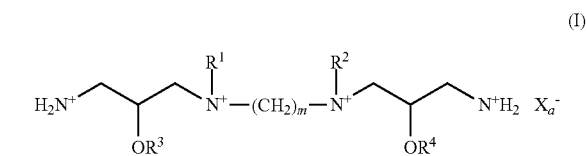

(I)

wherein $R^1$ and $R^2$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ and $R^4$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; m is an integer from 1 to 6; $X_a^-$ is an anion;

(ii) a second cationic lipid at a compositional molar ratio from about 0.24 to about 0.51 and of formula:

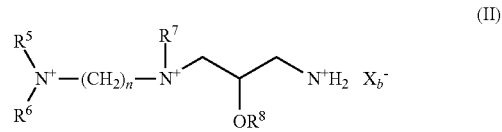

(II)

wherein $R^5$ and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^6$ and $R^7$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; n is an integer from 1 to 6; and $X_b^-$ is an anion;

(iii) a first helper lipid at a compositional molar ratio from about 0.20 to about 0.32;

(iv) a second helper lipid at a compositional molar ratio from about 0.01 to about 0.14; and (v) a biostability enhancing agent at a compositional molar ratio from about 0.01 to about 0.02.

In some embodiments, the nucleic acid encodes an engineered nuclease wherein the nuclease comprises a DNA binding domain and a cleavage domain. In other embodiments, the nucleic acid of the LNP encodes an engineered transcription factor comprising a DNA binding domain and transcriptional domain (e.g., activation or repression domain). In some aspects, the DNA binding domain is a zinc finger DNA binding domain, a TALE DNA binding domain, a RNA molecule (e.g., single guide (sg) RNA of a CRISPR/Cas nuclease), or a meganuclease DNA binding domain. In further aspects, the cleavage domain of the nuclease comprises a wild-type or an engineered (mutated) cleavage domain from an endonuclease, a meganuclease DNA cleavage domain, or a Cas DNA cleavage domain. In some embodiments, the DNA cleavage domain is FokI. In further embodiments, the FokI domain comprises mutations in the dimerization domain (see e.g. U.S. Pat. No. 8,623,618) or in the regions of the FokI domain that non-specifically interact with the phosphate backbone of the DNA molecule (See e.g. U.S. Patent Publication No. 2018/0087072). In certain embodiments, the nuclease binds to a target site in an intron and/or exon of a CFTR gene, for example a ZFNs comprising ZFPs, TALENs comprising TAL-effector domains and/or CRISPR/Cas nucleases comprising sgRNAs that bind to target sites of 9, 10, 11, 12, 13, 14, 15, 16, 17, 18 or more nucleotides of the target sites shown in Table 2; International Patent Publication No. WO 2018/204469 or U.S. Pat. No. 9,161,995.

In another aspect, fusion polypeptides comprising a DNA binding domain and an engineered cleavage half-domain as described herein are provided. In certain embodiments, the DNA-binding domain is a zinc finger binding domain (e.g., an engineered zinc finger binding domain). In other embodiments, the DNA-binding domain is a TALE DNA-binding domain. In still further embodiments, the DNA binding domain is a catalytically inactive Cas9 or Cfp1 protein (dCas9 or dCfp1). In some embodiments, the engineered cleavage half-domain forms a nuclease complex with a catalytically inactive engineered cleavage half-domain to form a nickase (see U.S. Pat. No. 9,200,266). In other embodiments, the ZFN, TALEN, and/or CRISPR/Cas system binds to and/or cleaves a safe-harbor gene, for example a CCR5 gene, a PPP1R12C (also known as AAVS1) gene, albumin, HPRT or a Rosa gene. See, e.g., U.S. Pat. Nos. 7,888,121; 7,972,854; 7,914,796; 7,951,925; 8,110,379; 8,409,861; 8,586,526; U.S. Patent Publication Nos. 2003/0232410; 2005/0208489; 2005/0026157; 2006/0063231;
2008/0159996; 2010/00218264; 2012/0017290; 2011/0265198; 2013/0137104;
2013/0122591; 2013/0177983; 2013/0177960; and 2014/0017212. The nucleases (or components thereof) may be provided as one or more polynucleotides encoding one or more ZFN, TALEN, and/or CRISPR/Cas system described herein, including one or more DNA-binding domains that bind to target sites in a CFTR gene, for example, a target site of 12 or more sequences in length as shown in Table 2; International Patent Publication No. WO 2018/204469 or U.S. Pat. No. 9,161,995. The polynucleotides may be, for example, mRNA. In some aspects, the mRNA may be chemically modified (See e.g. Kormann et al. (2011) *Nature Biotechnology* 29(2): 154-157). In other aspects, the mRNA may comprise an ARCA cap introduced during synthesis (see U.S. Pat. Nos. 7,074,596 and 8,153,773). In some aspects the mRNA may comprise a cap introduced by enzymatic modification. The enzymatically introduced cap may comprise Cap0, Cap1 or Cap2 (See e.g. Smietanski et al. (2014) *Nature Communications* 5:3004). In further aspects, the mRNA may be capped by chemical modification. In further embodiments, the mRNA may comprise a mixture of unmodified and modified nucleotides (see U.S. Patent Publication No. 2012/0195936). In still further embodiments, the mRNA may comprise a WPRE element (see U.S. Pat. No. 10,179,918), and in further embodiments, the WPRE element may be a mutated WPRE element (see e.g. Zanta-Boussif et al. (2009) *Gene Ther* 16(5):605-19). In some embodiments, the mRNA is double stranded (See e.g. Kariko et al. (2011) *Nucl Acid Res* 39:e142). In other embodiments the mRNA is single stranded. In some embodiments, the polyA track at the end of the message is extended. In preferred embodiments, the polyA track comprises 50 more polyAs, including for example, 50 (SEQ ID NO: 24), 51 (SEQ ID NO: 25) or 64 (SEQ ID NO: 26) poly As. In more preferred embodiments, the polyA track comprises 128 poly As (SEQ ID NO: 27), or comprises 193 poly As (SEQ ID NO: 29) or more. In preferred embodiments, the poly A track comprises 50, 51, 64, 70, 80, 90, 100, 110, 120, 128, 130, 140, 150, 160, 170, 180, 190, 193, 200 or more poly As. In other embodiments, some, most or all of the uridines in the wobble positions in the codons of the mRNAs are altered to another nucleotide. In some embodiments, 5%, 6%, 7%, 8%, 9%, 10%, 11%, 12%, 13%, 14%, 15% or more of the nucleotides in the wobble positions are altered.

The methods and compositions of the invention also include LNPs comprising ZFNs with mutations to amino acids within the ZFP DNA binding domain ("ZFP backbone") that can interact non-specifically with phosphates on the DNA backbone, but they do not comprise changes in the DNA recognition helices. Thus, the invention includes mutations of cationic amino acid residues in the ZFP backbone that are not required for nucleotide target specificity. See, e.g., U.S. Patent Publication No. 2018/0087072.

In some embodiments, the LNPs comprise a donor molecule (e.g., DNA or RNA). In some aspects, the donor is a plasmid, minicircle or a linear DNA. In further embodiments, the LNPs comprise both RNAs and DNAs. In some aspects, the RNAs and/or DNAs encode fusion molecules, and in some instances, the fusion molecules are engineered nucleases or engineered transcription factors. RNAs and DNAs may be provided in any combination, including but not limited to, RNA nuclease(s) and DNA donors, RNA nucleases and donors, RNA donors and DNA nucleases, and DNA nucleases and donors. In some embodiments, the RNAs provided encode specific nucleases for cleaving an endogenous gene, and the DNAs provided comprise transgene cassettes for insertion into the cleaved gene. The DNA or RNA transgenes can comprise an open reading frame encoding a therapeutic protein or mRNA of interest, and can further comprise regulatory sequences such as promoter sequences, and can still further comprise sequences associated with increased expression of the transgene including intron and enhancer sequences. In further embodiments, the promoter sequences have tissue specific expression patterns. In some embodiments, the DNA transgenes comprise homology arms to enhance nuclease-driven targeted integration. In other embodiments, the DNA or RNA transgene comprises a cDNA encoding a therapeutic protein, or may encode a RNA molecule of interest such as a shRNA, miRNA, RNAi etc. In further embodiments, the donor may be a cDNA that may comprise the full-length transgene, or may comprise a truncated or fragment of the transgene. In some embodiments, the transgene for insertion is a wild type gene for insertion into a cell that does not express a wild type version of the gene. In other embodiments, the transgene for insertion encodes an engineered therapeutic protein such as an antibody or a modified version of a therapeutic protein with improved qualities compared to the wild type version thereof.

Donor sequences can range in length from 50 to 5,000 nucleotides (or any integral value of nucleotides therebetween) or longer. In some embodiments, the donor comprises a full-length gene flanked by regions of homology with the targeted cleavage site. In some embodiments, the donor lacks homologous regions (homology arms) and is integrated into a target locus through homology independent mechanism (i.e. NHEJ). In other embodiments, the donor comprises a smaller piece of nucleic acid flanked by homologous regions for use in the cell (i.e. for gene correction via targeted integration). In some embodiments, the donor comprises a gene encoding a functional or structural component such as a shRNA, RNAi, miRNA or the like. In other embodiments, the donor comprises sequences encoding one or more regulatory elements that bind to and/or modulate expression of a gene of interest. In other embodiments, the donor is a regulatory protein of interest (e.g. ZFP TFs, TALE TFs and/or a CRISPR/Cas TF) that binds to and/or modulates expression of a gene of interest. In other embodiments, the donor is a sequence (e.g., oligonucleotide) that corrects a mutation in an endogenous gene, for example a mutation an endogenous CFTR gene (e.g., Δ508 mutation).

In some embodiments, the transgene encodes a protein for treatment of a patient in need thereof and is integrated using the methods and compositions of the invention into a safe harbor locus. In some aspects, the safe harbor is selected from AAVS1, albumin, HPRT or Rosa. The transgene may encode a protein such that the methods of the invention can be used for production of protein that is deficient or lacking (e.g., "protein replacement"). In some instances, the protein may be involved treatment for a lysosomal storage disease. Other therapeutic proteins may be expressed, including protein therapeutics for conditions as diverse as epidermolysis bullosa, cystic fibrosis or AAT deficient emphysema. In certain embodiments, the protein is a functional CFTR protein. In other aspects, the transgene may comprise sequences (e.g., engineered sequences) such that the expressed protein has characteristics which give it novel and desirable features (increased half-life, changed plasma clearance characteristics etc.). Engineered sequences can also include amino acids derived from the albumin sequence. In some aspects, the transgenes encode therapeutic proteins, therapeutic hormones, plasma proteins, antibodies and the like. In some embodiments, the protein is an engineered transcription factor, for example a repressor or an activator.

Also provided herein are cells that have been modified by the LNPs, virus, polypeptides and/or polynucleotides of the invention. In some embodiments, the cells comprise a nuclease-mediated insertion of a transgene, or a nuclease-mediated knock out of a gene. The modified cells, and any cells derived from the modified cells do not necessarily comprise the nucleases of the invention more than transiently, but the modifications mediated by such nucleases remain. In some embodiments, the cells can comprise, but are not limited to, mammalian cells, stem cells, embryonic stem cells, hematopoietic stem cells, pulmonary cells, pancreatic cells, hepatocytes, cells of the exocrine system (sweat glands), epithelial cells of the urogenital systems, and induced pluripotent stem cells. In the lung, the targeted cells can be epithelial cells lining the airways.

In yet another aspect, methods for targeted cleavage of cellular chromatin in a region of interest; methods of causing targeted alterations (e.g., insertions and/or deletions) to occur in a cell; methods of treating infection; and/or methods of treating disease (e.g., cystic fibrosis) are provided. These methods may be practiced in vitro, ex vivo or in vivo. The methods involve cleaving cellular chromatin at a predetermined region of interest in cells by introducing an LNP or composition comprising an LNP into the cells and expressing a pair of fusion polypeptides as described herein (i.e., a pair of fusion polypeptides in which one fusion polypeptide comprises the engineered cleavage half-domains as described herein). In certain embodiments, the targeted cleavage of the on-target site is increased by at least 50 to 200% (or any value therebetween) or more, including 50%-60% (or any value therebetween), 60%-70% (or any value therebetween), 70%-80% (or any value therebetween), 80%-90% (or any value therebetween, 90% to 200% (or any value therebetween), as compared to cleavage domains without the mutations as described herein. Similarly, using the methods and compositions as described herein, off-target site cleavage is reduced by 1-100 or more fold, including but not limited to 1-50 fold (or any value therebetween).

Targeted alterations include, but are not limited to, point mutations (i.e., conversion of a single base pair to a different base pair), substitutions (i.e., conversion of a plurality of base pairs to a different sequence of identical length), insertions or one or more base pairs, deletions of one or more base pairs and any combination of the aforementioned sequence alterations. Alterations can also include conversion of base pairs that are part of a coding sequence such that the encoded amino acid is altered. Alternations can be facilitated by homology-directed repair mechanisms or non-homology directed repair mechanisms.

A composition (e.g., pharmaceutical composition) comprising one or more of any of the LNPs and/or donor polynucleotides described herein is also provided. In some embodiments, the composition comprises one or more types of LNPs where each LNP type comprises alternate nucleic acids and/or alternate cationic lipids. In some embodiments the LNP comprises an LNP as disclosed in U.S. Patent Publication No. 2019/0060482, and hereby explicitly incorporated by reference in its entirety as though fully set forth herein.

In some instances, the composition further comprises a viral particle. In some aspects, the viral particle is an AAV, adenovirus, lentivirus or the like. In some embodiments, the virus comprises a DNA, while in further embodiments, the LNP comprises mRNAs and the virus comprises a DNA donor as described herein. Especially preferred are compositions comprising an LNP comprising mRNAs encoding a nuclease, and an AAV comprising a DNA donor. In some aspects, the nuclease is an engineered nuclease (e.g., a ZFN, TALEN, MegaTAL, meganuclease, or TtAgo or CRISPR/Cas system).

In some embodiments, the composition of the invention comprises additional compositions such as buffers, stabilizers, etc.

In some embodiments, the composition comprising the LNPs comprising mRNA encoding a fusion molecule is administered to a patient in need thereof as a single dose. In other embodiments, the composition is administered to a patient 1, 2, 3 or more times. In some embodiments, the composition is administered to a patient and then re-administered 7, 14, 21, 28, 30, 40, 50, 75, 100, 200 or more days after the first administration. In further embodiments, additional administration is performed 1, 2, 5, or 10 years following the first administration, or following the one or more administrations done in the first year.

The LNPs (and compositions comprising the LNPs) of the invention can be used for treatment of a patient in need thereof. Thus, the invention comprises methods for treating a patient in need thereof wherein the method comprises formulating a composition comprising the LNPs of the invention and administering the composition to a patient such that a disease (e.g., CF) is prevented or treated. In other embodiments, the LNPs of the invention can be used for transduction of cells in vitro. Thus, the invention comprises methods for transducing a cell with LNPs, optionally formulated as a composition, to introduce the gene therapy reagents of the invention into the cell. The LNPs as described herein may be administered sequentially and/or repeatedly, including but not limited to, administration of an LNP nuclease before and/or after administration of an LNP donor.

In another aspect, described herein is a kit comprising LNPs comprising nucleic acids as described herein (e.g., a fusion molecule as described herein or a polynucleotide encoding one or more zinc finger proteins, cleavage domains, transcriptional activation or repression domains and/or fusion molecules as described herein; virus comprising donors of interest as described herein, ancillary reagents; and optionally instructions and suitable containers. The kit may also include one or more nucleases or polynucleotides encoding such nucleases.

BRIEF DESCRIPTION OF THE DRAWINGS

FIG. 1A is a graph showing indel levels from sorted lung CD326+ epithelial cells harvested from individual mice treated with PBS, 0.3, 1, or 2 mg/kg ZFN mRNA-LNP. Each dot represents data from a single mouse. FIG. 1B similarly shows indel levels from dissociated, unsorted lung cells harvested from individual mice treated with PBS, 0.3, 1, or 2 mg/kg ZFN mRNA-LNP. Each dot represents data from a single mouse. FIG. 1C shows indel levels from sorted lung CD45+ immune cells harvested from individual mice treated with PBS, 0.3, 1, or 2 mg/kg ZFN mRNA-LNP. Each dot represents data from a single mouse. FIG. 1D shows indel levels from sorted lung CD31+ endothelial cells harvested from individual mice treated with PBS, 0.3, 1, or 2 mg/kg ZFN mRNA-LNP. Each dot represents data from a single mouse. FIG. 1E shows indel levels from bulk liver tissue harvested from individual mice treated with PBS, 0.3, 1, or 2 mg/kg ZFN mRNA-LNP. Each dot represents data from a single mouse.

DETAILED DESCRIPTION

Figure 1A:
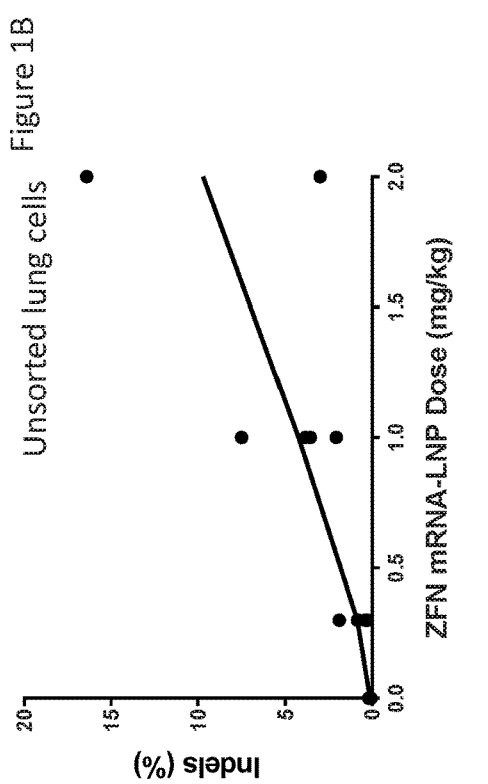
FIGS. 1A through 1E depict the ZFN activity (as measured by insertions and/or deletions known as "indels") in cells of the lung and liver following intravenous injection of live mice with LNPs comprising mRNAs that encode ZFNs specific for mouse CFTR intron 1.

Disclosed herein are methods and compositions for delivery of nucleases to cells. Embodiments of the LNPs are used to deliver mRNAs encoding the nucleases in vivo to treat cystic fibrosis. In animals, the LNPs can be co-dosed with a donor such that the nuclease delivered via the LNP can directed targeted integration of the donor.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al., MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

A "gene therapy reagent" or "gene therapy polynucleotide" is a reagent used to modulate gene expression in a cell. Gene therapy reagents can comprise nucleases and transcription factors where the reagents interact with a gene to modulate its expression. In some embodiments, the nucleases are engineered to cleave a specific sequence in a gene, and in other embodiments, engineered transcription factors are used to activate or repress a desired gene. In some embodiments, gene therapy reagents can also comprise specific donor molecules, for example, a transgene encoding a therapeutic protein, fragments of a transgene, nucleases or transcription factors.

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide," and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$. "Non-specific binding" refers to, non-covalent interactions that occur between any molecule of interest (e.g. an engineered nuclease) and a macromolecule (e.g. DNA) that are not dependent on-target sequence.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity. In the case of an RNA-guided nuclease system, the RNA guide is heterologous to the nuclease component (Cas9 or Cfp1) and both may be engineered.

A "DNA binding molecule" is a molecule that can bind to DNA. Such DNA binding molecule can be a polypeptide, a domain of a protein, a domain within a larger protein or a polynucleotide. In some embodiments, the polynucleotide is DNA, while in other embodiments, the polynucleotide is RNA. In some embodiments, the DNA binding molecule is a protein domain of a nuclease (e.g. the FokI domain), while in other embodiments, the DNA binding molecule is a guide RNA component of an RNA-guided nuclease (e.g. Cas9 or Cfp1).

A "DNA binding protein" (or binding domain) is a protein, or a domain within a larger protein, that binds DNA in a sequence-specific manner, for example through one or more zinc fingers or through interaction with one or more RVDs in a zinc finger protein or TALE, respectively. The term zinc finger DNA binding protein is often abbreviated as zinc finger protein or ZFP.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains, each comprising a repeat variable diresidue (RVD), are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. TALE proteins may be designed to bind to a target site using canonical or non-canonical RVDs within the repeat units. See, e.g., U.S. Pat. Nos. 8,586,526 and 9,458,205, each incorporated by reference herein in its entirety.

Zinc finger and TALE DNA-binding domains can be "engineered" to bind to a predetermined nucleotide sequence, for example via engineering (altering one or more amino acids) of the recognition helix region of a naturally occurring zinc finger protein or by engineering of the amino acids involved in DNA binding (the "repeat variable diresidue" or RVD region). Therefore, engineered zinc finger proteins or TALE proteins are proteins that are non-naturally occurring. Non-limiting examples of methods for engineering zinc finger proteins and TALEs are design and selection. A designed protein is a protein not occurring in nature whose design/composition results principally from rational criteria. Rational criteria for design include application of substitution rules and computerized algorithms for processing information in a database storing information of existing ZFP or TALE designs and binding data. See, for example, U.S. Pat. Nos. 9,458,205; 8,586,526; 6,140,081; 6,453,242; and 6,534,261; see also International Patent Publication Nos. WO 98/53058; WO 98/53059; WO 98/53060; WO 02/016536; and WO 03/016496.

A "selected" zinc finger protein, TALE protein or CRISPR/Cas system is not found in nature whose production results primarily from an empirical process such as phage display, interaction trap, or hybrid selection. See e.g., U.S. Pat. Nos. 5,789,538; 5,925,523; 6,007,988; 6,013,453; 6,200,759; International Patent Publication Nos. WO 95/19431; WO 96/06166; WO 98/53057; WO 98/54311; WO 00/27878; WO 01/60970; WO 01/88197; and WO 02/099084.

"TtAgo" is a prokaryotic Argonaute protein thought to be involved in gene silencing. TtAgo is derived from the bacteria *Thermus thermophilus*. See, e.g. Swarts et al., ibid; G. Sheng et al. (2013) *Proc. Natl. Acad. Sci. U.S.A.* 111: 652). A "TtAgo system" is all the components required including e.g. guide DNAs for cleavage by a TtAgo enzyme.

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In certain methods of the disclosure, one or more targeted nucleases as described herein create a double-stranded break (DSB) in the target sequence (e.g., cellular chromatin) at a predetermined site (e.g., a gene or locus of interest). The DSB mediates integration of a construct (e.g. donor) as described herein and a "donor" polynucleotide, having homology to the nucleotide sequence in the region of the break, can be introduced into the cell. The presence of the DSB has been shown to facilitate integration of the donor sequence. Optionally, the construct has homology to the nucleotide sequence in the region of the break. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional engineered nucleases can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Pat. Nos. 7,888,121; 7,914,796; 8,034,598; 8,623,618 and U.S. Patent Publication No. 2011/0201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 100,000,000 nucleotides in length (or any integer value therebetween), preferably between about 100 and 100,000 nucleotides in length (or any integer therebetween), more preferably between about 2000 and 20,000 nucleotides in length (or any value therebetween) and even more preferable, between about 5 and 15 kb (or any value therebetween).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome" is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids, minicircles and certain viral genomes. The liver specific constructs described herein may be epiosomally maintained or, alternatively, may be stably integrated into the cell.

An "exogenous" molecule is a molecule that is not normally present in a cell but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, ligases, deubiquitinases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule or can be different chemical types of molecules. Examples of fusion molecules include, but are not limited to, fusion proteins (for example, a fusion between a ZFP or TALE DNA-binding domain and one or more activation domains) and fusion nucleic acids (for example, a nucleic acid encoding the fusion protein described supra) or CRISPR/Cas nuclease or transcription factor systems in which a single guide RNA DNA-binding domain is associated with one or more functional domains (e.g., cleavage domains, transcriptional activation or repression domains, etc.). Examples of the second type of fusion molecule include, but are not limited to, a fusion between a triplex-forming nucleic acid and a polypeptide, and a fusion between a minor groove binder and a nucleic acid. The term also includes systems in which a polynucleotide component associates with a polypeptide component to form a functional molecule (e.g., a CRISPR/Cas system in which a single guide RNA associates with a functional domain to modulate gene expression).

Expression of a fusion molecule in a cell can result from delivery of the fusion molecule to the cell or by delivery of a polynucleotide encoding the fusion molecule to a cell, wherein the polynucleotide is transcribed, and the transcript is translated, to generate the fusion molecule. Trans-splicing, polypeptide cleavage and polypeptide ligation can also be involved in expression of a protein in a cell. Methods for polynucleotide and polypeptide delivery to cells are presented elsewhere in this disclosure.

A "gene" for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" or "modification" of gene expression refers to a change in the activity of a gene. Modulation of expression can include, but is not limited to, gene activation and gene repression, including by modification of the gene via binding of an exogenous molecule (e.g., engineered transcription factor). Modulation may also be achieved by modification of the gene sequence via genome editing (e.g., cleavage, alteration, inactivation, random mutation). Gene inactivation refers to any reduction in gene expression as compared to a cell that has not been modified as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

A "safe harbor" locus is a locus within the genome wherein a gene may be inserted without any deleterious effects on the host cell. Most beneficial is a safe harbor locus in which expression of the inserted gene sequence is not perturbed by any read-through expression from neighboring genes. Non-limiting examples of safe harbor loci that are targeted by nuclease(s) include CCR5, CCR5, HPRT, AAVS1, Rosa and albumin. See, e.g., U.S. Pat. Nos. 7,951, 925; 8,771,985; 8,110,379; 7,951,925; U.S. Patent Publication Nos. 2010/0218264; 2011/0265198; 2013/0137104; 2013/0122591; 2013/0177983; 2013/0177960; 2015/0056705; and 2015/0159172.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

"Eukaryotic" cells include, but are not limited to, fungal cells (such as yeast), plant cells, animal cells, mammalian cells and human cells (e.g., T-cells), including stem cells (pluripotent and multipotent).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid or protein (e.g., coding function, ability to hybridize to another nucleic acid, enzymatic activity assays) are well-known in the art.

A polynucleotide "vector" or "construct" is capable of transferring gene sequences to target cells. Typically, "vector construct," "expression vector," "expression construct," "expression cassette," and "gene transfer vector," mean any nucleic acid construct capable of directing the expression of a gene of interest and which can transfer gene sequences to target cells. Thus, the term includes cloning, and expression vehicles, as well as integrating vectors.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the expression cassettes of the invention can be administered. Subjects of the present invention include those with a disorder or those at risk for developing a disorder.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease. An "intended" or "on-target" sequence is the sequence to which the binding molecule is intended to bind and an "unintended" or "off-target" sequence includes any sequence bound by the binding molecule that is not the intended target.

The term "lipid" refers to a group of organic compounds that include, but are not limited to, esters of fatty acids and are generally characterized by being poorly soluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

A "steroid" is a compound comprising the following carbon skeleton:

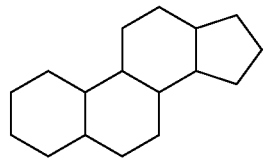 [SMILES: C1CCC2C(C1)CCC1C3CCCC3CCC21]

Non-limiting examples of steroids include cholesterol, and the like.

A "cationic lipid" refers to a lipid capable of being positively charged. Exemplary cationic lipids include one or more amine group(s) which bear the positive charge. Preferred cationic lipids are ionizable such that they can exist in a positively charged or neutral form depending on pH. The ionization of the cationic lipid affects the surface charge of the lipid nanoparticle under different pH conditions. This charge state can influence plasma protein absorption, blood clearance and tissue distribution (Semple, S. C., et al. (1998) *Adv. Drug Deliv Rev* 32:3-17) as well as the ability to form endosomolytic non-bilayer structures (Hafez, I. M., et al. (2001) *Gene Ther* 8:1188-1196) critical to the intracellular delivery of nucleic acids.

The term "lipid nanoparticle" refers to particles having at least one dimension on the order of nanometers (e.g., 1-1,000 nm) which can include one or more cationic lipids. In some embodiments, lipid nanoparticles are included in a formulation that can be used to deliver an active agent or therapeutic agent, such as a nucleic acid (e.g., mRNA) to a target site of interest (e.g., cell, tissue, organ, tumor, and the like). In some embodiments, the lipid nanoparticles of the invention comprise a nucleic acid. Such lipid nanoparticles typically comprise a cationic lipid and one or more excipient selected from neutral lipids, charged lipids, steroids and polymer conjugated lipids. In some embodiments, the active agent or therapeutic agent, such as a nucleic acid, may be encapsulated in the lipid portion of the lipid nanoparticle or an aqueous space enveloped by some or all of the lipid portion of the lipid nanoparticle, thereby protecting it from enzymatic degradation or other undesirable effects induced by the mechanisms of the host organism or cells e.g. an adverse immune response.

In various embodiments, the lipid nanoparticles have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In certain embodiments, nucleic acids, when present in the lipid nanoparticles, are resistant in aqueous solution to degradation with a nuclease. Lipid nanoparticles comprising nucleic acids, cationic lipids, pegylated lipids and their method of preparation are disclosed in, e.g., U.S. Patent Publication Nos. 2004/0142025, 2007/0042031 and International Patent Publication Nos. WO 2013/016058; WO 2013/086373; WO 2015/199952; WO 2017/004143; and WO 2017/075531, the full disclosures of which are herein incorporated by reference in their entirety for all purposes.

The term "polymer conjugated lipid" refers to a molecule comprising both a lipid portion and a polymer portion. An example of a polymer conjugated lipid is a pegylated lipid. The term "pegylated lipid" refers to a molecule comprising both a lipid portion and a polyethylene glycol portion.

The term "neutral lipid" refers to any of a number of lipid species that exist either in an uncharged or neutral zwitterionic form at a selected pH. At physiological pH, such lipids include, but are not limited to, phosphotidylcholines such as 1,2-Distearoyl-sn-glycero-3-phosphocholine (DSPC), 1,2-Dipalmitoyl-sn-glycero-3-phosphocholine (DPPC), 1,2-Dimyristoyl-sn-glycero-3-phosphocholine (DMPC), 1-Palmitoyl-2-oleoyl-sn-glycero-3-phosphocholine (POPC), 1,2-dioleoyl-sn-glycero-3-phosphocholine (DOPC), phophatidylethanolamines such as 1,2-Dioleoyl-sn-glycero-3-phosphoethanolamine (DOPE), sphingomyelins (SM), ceramides, steroids such as sterols and their derivatives. Neutral lipids may be synthetic or naturally derived.

The term "charged lipid" refers to any of a number of lipid species that exist in either a positively charged or negatively charged form independent of the pH within a useful physiological range e.g. pH ~3 to pH ~9. Charged lipids may be synthetic or naturally derived. Examples of charged lipids include phosphatidylserines, phosphatidic acids, phosphatidylglycerols, phosphatidylinositols, sterol hemi succinates, dialkyl trimethylammonium-propanes, (e.g. DOTAP, DOTMA), dialkyl dimethylaminopropanes, ethyl phosphocholines, dimethylaminoethane carbamoyl sterols (e.g. DC-Chol).

"Alkyl" refers to a straight or branched hydrocarbon chain radical consisting solely of carbon and hydrogen atoms, which is saturated or unsaturated (i.e., contains one or more double and/or triple bonds), having from one to twenty-four carbon atoms (C1-C24 alkyl), one to twelve carbon atoms (C1-C12 alkyl), one to eight carbon atoms (C1-C8 alkyl) or one to six carbon atoms (C1-C6 alkyl) and which is attached to the rest of the molecule by a single bond, e.g., methyl, ethyl, n propyl, 1 methylethyl (iso propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group is optionally substituted.

"Cycloalkyl" or "carbocyclic ring" refers to a stable non aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7 dimethyl bicyclo[2.2.1]heptanyl, and the like. Unless otherwise stated specifically in the specification, a cycloalkyl group is optionally substituted.

"Heterocyclyl" or "heterocyclic ring" refers to a stable 3 to 18 membered non aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2 oxopiperazinyl, 2 oxopiperidinyl, 2 oxopyrrolidinyl, oxazolidinyl, piperidinyl, piperazinyl, 4 piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1 oxo thiomorpholinyl, and 1,1 dioxo thiomorpholinyl. Unless stated otherwise specifically in the specification, a heterocyclyl group may be optionally substituted.

The term "substituted" used herein means any of the above groups (e.g., alkyl, cycloalkyl or heterocyclyl) wherein at least one hydrogen atom is replaced by a bond to a non-hydrogen atoms such as, but not limited to: a halogen atom such as F, Cl, Br, and I; oxo groups (=O); hydroxyl groups (—OH); alkoxy groups (ORa, where Ra is C1-C12 alkyl or cycloalkyl); carboxyl groups (OC(=O)Ra or —C(=O)ORa, where Ra is H, C1-C12 alkyl or cycloalkyl); amine groups (NRaRb, where Ra and Rb are each independently H, C1-C12 alkyl or cycloalkyl); C1-C12 alkyl groups; and cycloalkyl groups. In some embodiments the substituent is a C1-C12 alkyl group. In other embodiments, the substituent is a cycloalkyl group. In other embodiments, the substituent is a halo group, such as fluoro. In other embodiments, the substituent is an oxo group. In other embodiments, the substituent is a hydroxyl group. In other embodiments, the substituent is an alkoxy group. In other embodiments, the substituent is a carboxyl group. In other embodiments, the substituent is an amine group.

"Optional" or "optionally" (e.g., optionally substituted) means that the subsequently described event of circumstances may or may not occur, and that the description includes instances where said event or circumstance occurs and instances in which it does not. For example, "optionally substituted alkyl" means that the alkyl radical may or may not be substituted and that the description includes both substituted alkyl radicals and alkyl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2 dimethylaminoethanol, 2 diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N ethylpiperidine, polyamine resins and the like. Particularly preferred organic bases are isopropylamine, diethylamine, ethanolamine, trimethylamine, dicyclohexylamine, choline and caffeine.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to that amount of a compound of the invention which, when administered to a mammal, preferably a human, is sufficient to effect treatment in the mammal, preferably a human. The amount of a lipid nanoparticle of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians. Cancer, monogenic diseases and graft versus host disease are non-limiting examples of conditions that may be treated using the compositions and methods described herein.

The cationic lipids or their pharmaceutically acceptable salts may contain one or more asymmetric centers and may thus give rise to enantiomers, diastereomers, and other stereoisomeric forms that may be defined, in terms of absolute stereochemistry, as (R) or (5) or, as (D) or (L) for amino acids. The present invention is meant to include all such possible isomers, as well as their racemic and optically pure forms. Optically active (+) and (−), (R) and (5), or (D) and (L) isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

The "wobble position" is defined as the third nucleotide in an mRNA encoding a codon which can be changed (substituted) with an alternative nucleotide without changing the identity of the resulting amino acid once translated.

DNA-Binding Molecules and Domains

Described herein are compositions comprising a DNA-binding domain that specifically binds to a target site in any gene or locus of interest. Any DNA-binding domain can be used in the compositions and methods disclosed herein, including but not limited to a zinc finger DNA-binding domain, a TALE DNA binding domain, the DNA-binding portion (sgRNA) of a CRISPR/Cas nuclease, or a DNA-binding domain from a meganuclease.

In certain embodiments, the DNA binding domain comprises a zinc finger protein. Preferably, the zinc finger protein is non-naturally occurring in that it is engineered to bind to a target site of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties. In certain embodiments, the DNA-binding domain comprises a zinc finger protein disclosed in U.S. Patent Publication No. 2012/0060230 (e.g., Table 1), incorporated by reference in its entirety herein.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as International Patent Publication Nos. WO 98/37186; WO 98/53057; WO 00/27878; WO 01/88197 and GB 2,338,237. In addition, enhancement of binding specificity for zinc finger binding domains has been described, for example, in U.S. Pat. No. 6,794,136.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. In addition, enhancement of binding specificity for zinc finger binding domains has been described, for example, in U.S. Pat. No. 6,794,136.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970; WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Usually, the ZFPs of the LNPs described herein include at least three fingers. Certain of the ZFPs include four, five or six fingers. The ZFPs that include three fingers typically recognize a target site that includes 9 or 10 nucleotides; ZFPs that include four fingers typically recognize a target site that includes 12 to 14 nucleotides; while ZFPs having six fingers can recognize target sites that include 18 to 21 nucleotides. The ZFPs can also be fusion proteins that include one or more regulatory domains, which domains can be transcriptional activation or repression domains.

ZFN-LNPs as described herein can include ZFNs in which the ZFP is further altered to increase its specificity for its intended target relative to other unintended cleavage sites, known as off-target sites, for example by introduction of mutations to the ZFP backbone as described in U.S. Patent Publication No. 2018/0087072. Thus, the engineered repressors and/or engineered nucleases described herein can comprise mutations in one or more of their DNA binding domain backbone regions and/or one or more mutations in their transcriptional regulatory domains. These ZFPs can include mutations to amino acids within the ZFP DNA binding domain ('ZFP backbone') to remove amino acid residues that can interact non-specifically with phosphates on the DNA backbone, but they do not comprise changes in the DNA recognition helices. Thus, the invention includes mutations of cationic amino acid residues in the ZFP backbone that are not required for nucleotide target specificity. In some embodiments, these mutations in the ZFP backbone comprise mutating a cationic amino acid residue to a neutral or anionic amino acid residue. In some embodiments, these mutations in the ZFP backbone comprise mutating a polar amino acid residue to a neutral or non-polar amino acid residue. In preferred embodiments, mutations are made at position (−5), (−9) and/or position (−14) relative to the DNA binding helix. In some embodiments, a zinc finger may comprise one or more mutations at (−5), (−9) and/or (−14). In further embodiments, one or more zinc finger in a multi-finger zinc finger protein may comprise mutations in (−5), (−9) and/or (−14). In some embodiments, the amino acids at (−5), (−9) and/or (−14) (e.g. an arginine (R) or lysine (K)) are mutated to an alanine (A), leucine (L), Ser (S), Asp (N), Glu (E), Tyr (Y) and/or glutamine (Q). In other embodiments, the fusion polypeptides can comprise mutations in the zinc finger DNA binding domain where the amino acids at the (−5), (−9) and/or (−14) positions are changed to any of the above listed amino acids in any combination (see e.g. U.S. Patent Publication No. 2018/0087072).

In some embodiments, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22:1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659;

Paques et al. (2007) *Current Gene Therapy* 7:49-66; U.S. Patent Publication No. 2007/0117128.

In other embodiments, the DNA binding domain comprises an engineered domain from a Transcriptional Activator-Like (TAL) effector (TALE) similar to those derived from the plant pathogens *Xanthomonas* (see Boch et al. (2009) *Science* 326:1509-1512 and Moscou and Bogdanove (2009) *Science* 326:1501) and Ralstonia (see Heuer et al. (2007) *Applied and Environmental Microbiology* 73(13): 4379-4384); U.S. Patent Publication Nos. 2011/0301073 and 2011/0145940. The plant pathogenic bacteria of the genus *Xanthomonas* are known to cause many diseases in important crop plants. Pathogenicity of *Xanthomonas* depends on a conserved type III secretion (T3 S) system which injects more than 25 different effector proteins into the plant cell. Among these injected proteins are transcription activator-like effectors (TALE) which mimic plant transcriptional activators and manipulate the plant transcriptome (see Kay et al. (2007) *Science* 318:648-651). These proteins contain a DNA binding domain and a transcriptional activation domain. One of the most well characterized TALEs is AvrBs3 from *Xanthomonas campestgris* pv. *Vesicatoria* (see Bonas et al. (1989) *Mol Gen Genet* 218:127-136 and International Patent Publication No. WO 2010/079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S., et al. (2006) *J. Plant Physiol* 163(3):256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al. (2007) *Appl and Envir Micro* 73(13):4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

Specificity of these TAL effectors depends on the sequences found in the tandem repeats. The repeated sequence comprises approximately 102 base pairs and the repeats are typically 91-100% homologous with each other (Bonas et al., ibid). Polymorphism of the repeats is usually located at positions 12 and 13 and there appears to be a one-to-one correspondence between the identity of the hypervariable diresidues (the repeat variable diresidue or RVD region) at positions 12 and 13 with the identity of the contiguous nucleotides in the TAL-effector's target sequence (see Moscou and Bogdanove (2009) *Science* 326: 1501 and Boch et al. (2009) *Science* 326:1509-1512). Experimentally, the natural code for DNA recognition of these TAL-effectors has been determined such that an HD sequence at positions 12 and 13 (Repeat Variable Diresidue or RVD) leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al., ibid). Engineered TAL proteins have been linked to a FokI cleavage half domain to yield a TAL effector domain nuclease fusion (TALEN), including TALENs with atypical RVDs. See, e.g., U.S. Pat. No. 8,586,526.

In some embodiments, the TALEN comprises an endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel et al. (2013) *Nucl Acid Res:*1-13, doi:10.1093/nar/gkt1224).

In still further embodiments, the nuclease comprises a compact TALEN. These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley et al. (2013) *Nat Comm* 4:1762, DOI: 10.1038/ncomms2782). In addition, the nuclease domain may also exhibit DNA-binding functionality. Any TALENs may be used in combination with additional TALENs (e.g., one or more TALENs (cTALENs or FokI-TALENs) with one or more mega-TALEs.

In addition, as disclosed in these and other references, zinc finger domains and/or multi-fingered zinc finger proteins or TALEs may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. In addition, enhancement of binding specificity for zinc finger binding domains has been described, for example, in U.S. Pat. No. 6,794,136. In certain embodiments, the DNA-binding domain is part of a CRISPR/Cas nuclease system, including a single guide RNA (sgRNA) DNA binding molecule that binds to DNA. See, e.g., U.S. Pat. No. 8,697,359 and U.S. Patent Publication Nos. 2015/0056705 and 2015/0159172. The CRISPR (clustered regularly interspaced short palindromic repeats) locus, which encodes RNA components of the system, and the cas (CRISPR-associated) locus, which encodes proteins (Jansen et al. (2002) *Mol. Microbiol.* 43:1565-1575; Makarova et al. (2002) *Nucleic Acids Res.* 30:482-496; Makarova et al. (2006) *Biol. Direct* 1:7; Haft et al. (2005) *PLoS Comput. Biol.* 1:e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

In some embodiments, the DNA binding domain is part of a TtAgo system (see Swarts et al., ibid; Sheng et al., ibid). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) *Science* 344: 972-973). In contrast, prokaryotic Ago proteins bind to small single-stranded DNA fragments and likely function to detect and remove foreign (often viral) DNA (Yuan et al. (2005) *Mol. Cell* 19:405; Olovnikov et al. (2013) *Mol. Cell* 51:594; Swarts et al., ibid). Exemplary prokaryotic Ago proteins include those from *Aquifex aeolicus, Rhodobacter sphaeroides*, and *Thermus thermophilus*.

One of the most well-characterized prokaryotic Ago protein is the one from *T. thermophilus* (TtAgo; Swarts et al., ibid). TtAgo associates with either 15 nt or 13-25 nt single-stranded DNA fragments with 5' phosphate groups. This "guide DNA" bound by TtAgo serves to direct the protein-DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G. Sheng et al., ibid). Ago from *Rhodobacter sphaeroides* (RsAgo) has similar properties (Olovnikov et al., ibid).

Exogenous guide DNAs of arbitrary DNA sequence can be loaded onto the TtAgo protein (Swarts et al., ibid.). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have improved activity at 37° C. Ago-RNA-mediated DNA cleavage could be used to affect a panopoly of outcomes including gene knock-out, targeted gene addition, gene correction, targeted gene deletion using techniques standard in the art for exploitation of DNA breaks.

Thus, any DNA-binding domain can be used.

Fusion Molecules

LNPs as describe herein can include fusion molecules comprising DNA-binding domains (e.g., ZFPs or TALEs, CRISPR/Cas components such as single guide RNAs) and a heterologous regulatory (functional) domain (or functional fragment thereof) are also provided. Common domains include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases) and their associated factors and modifiers. U.S. Patent Publication Nos. 2005/0064474; 2006/0188987; and 2007/0218528 for details regarding fusions of DNA-binding domains and nuclease cleavage domains, incorporated by reference in their entireties herein.

Suitable domains for achieving activation include the HSV VP16 activation domain (see, e.g., Hagmann et al. (1997) *J. Virol.* 71:5952-5962) nuclear hormone receptors (see, e.g., Torchia et al. (1998) *Curr. Opin. Cell. Biol.* 10:373-383); the p65 subunit of nuclear factor kappa B (Bitko & Barik (1998) *J. Virol.* 72:5610-5618 and Doyle & Hunt (1997) *Neuroreport* 8:2937-2942); Liu et al. (1998) *Cancer Gene Ther.* 5:3-28), or artificial chimeric functional domains such as VP64 (Beerli et al. (1998) *Proc. Natl. Acad. Sci. USA* 95:14623-33), and degron (Molinari et al. (1999) *EMBO J.* 18:6439-6447). Additional exemplary activation domains include, Oct 1, Oct-2A, Sp1, AP-2, and CTF1 (Seipel et al. (1992) *EMBO J.* 11:4961-4968 as well as p300, CBP, PCAF, SRC1 PvALF, AtHD2A and ERF-2. See, for example, Robyr et al. (2000) *Mol. Endocrinol.* 14:329-347; Collingwood et al. (1999) *J. Mol. Endocrinol.* 23:255-275; Leo et al. (2000) *Gene* 245:1-11; Manteuffel-Cymborowska (1999) *Acta Biochim. Pol.* 46:77-89; McKenna et al. (1999) *J. Steroid Biochem. Mol. Biol.* 69:3-12; Malik et al. (2000) *Trends Biochem. Sci.* 25:277-283; and Lemon et al. (1999) *Curr. Opin. Genet. Dev.* 9:499-504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) *Gene* 245:21-29; Okanami et al. (1996) *Genes Cells* 1:87-99; Goff et al. (1991) *Genes Dev.* 5:298-309; Cho et al. (1999) *Plant Mol. Biol.* 40:419-429; Ulmason et al. (1999) *Proc. Natl. Acad. Sci. USA* 96:5844-5849; Sprenger-Haussels et al. (2000) *Plant J.* 22:1-8; Gong et al. (1999) *Plant Mol. Biol.* 41:33-44; and Hobo et al. (1999) *Proc. Natl. Acad. Sci. USA* 96:15,348-15,353.

It will be clear to those of skill in the art that, in the formation of a fusion molecule (or a nucleic acid encoding same) between a DNA-binding domain and a functional domain, either an activation domain or a molecule that interacts with an activation domain is suitable as a functional domain. Essentially any molecule capable of recruiting an activating complex and/or activating activity (such as, for example, histone acetylation) to the target gene is useful as an activating domain of a fusion molecule. Insulator domains, localization domains, and chromatin remodeling proteins such as ISWI-containing domains and/or methyl binding domain proteins suitable for use as functional domains in fusion molecules are described, for example, in U.S. Patent Publication Nos. 2002/0115215 and 2003/0082552 and in International Patent Publication No. WO 02/44376.

Exemplary repression domains include, but are not limited to, KRAB A/B, KOX, TGF-beta-inducible early gene (TIEG), v-erbA, SID, MBD2, MBD3, members of the DNMT family (e.g., DNMT1, DNMT3A, DNMT3B), Rb, and MeCP2. See, for example, Bird et al. (1999) *Cell* 99:451-454; Tyler et al. (1999) *Cell* 99:443-446; Knoepfler et al. (1999) *Cell* 99:447-450; and Robertson et al. (2000) *Nature Genet.* 25:338-342. Additional exemplary repression domains include, but are not limited to, ROM2 and AtHD2A. See, for example, Chem et al. (1996) *Plant Cell* 8:305-321; and Wu et al. (2000) *Plant J.* 22:19-27.

Fusion molecules are constructed by methods of cloning and biochemical conjugation that are well known to those of skill in the art. Fusion molecules comprise a DNA-binding domain and a functional domain (e.g., a transcriptional activation or repression domain). Fusion molecules also optionally comprise nuclear localization signals (such as, for example, that from the SV40 medium T-antigen) and epitope tags (such as, for example, FLAG and hemagglutinin). Fusion molecules (and nucleic acids encoding them) are designed such that the translational reading frame is preserved among the components of the fusion.

Fusions between a polypeptide component of a functional domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, Ill.) Catalogue. Methods and compositions for making fusions between a minor groove binder and a polypeptide have been described. Mapp et al. (2000) *Proc. Natl. Acad. Sci. USA* 97:3930-3935. Furthermore, single guide RNAs of the CRISPR/Cas system associate with functional domains to form active transcriptional regulators and nucleases.

In certain embodiments, the target site is present in an accessible region of cellular chromatin. Accessible regions can be determined as described, for example, in U.S. Pat. Nos. 7,217,509 and 7,923,542. If the target site is not present in an accessible region of cellular chromatin, one or more accessible regions can be generated as described in U.S. Pat. Nos. 7,785,792 and 8,071,370. In additional embodiments, the DNA-binding domain of a fusion molecule is capable of binding to cellular chromatin regardless of whether its target site is in an accessible region or not. For example, such DNA-binding domains are capable of binding to linker DNA and/or nucleosomal DNA. Examples of this type of "pioneer" DNA binding domain are found in certain steroid receptor and in hepatocyte nuclear factor 3 (HNF3) (Cordingley et al. (1987) *Cell* 48:261-270; Pina et al. (1990) *Cell* 60:719-731; and Cirillo et al. (1998) *EMBO J.* 17:244-254).

The fusion molecule may be formulated with a pharmaceutically acceptable carrier, as is known to those of skill in the art. See, for example, Remington's Pharmaceutical Sciences, 17th ed., 1985; and U.S. Pat. Nos. 6,453,242 and 6,534,261.

The functional component/domain of a fusion molecule can be selected from any of a variety of different components capable of influencing transcription of a gene once the fusion molecule binds to a target sequence via its DNA binding domain. Hence, the functional component can include, but is not limited to, various transcription factor domains, such as activators, repressors, co-activators, co-repressors, and silencers.

Additional exemplary functional domains are disclosed, for example, in U.S. Pat. Nos. 6,534,261 and 6,933,113.

Functional domains that are regulated by exogenous small molecules or ligands may also be selected for use in the LNPs described herein. For example, RheoSwitch® technology may be employed wherein a functional domain only assumes its active conformation in the presence of the external RheoChem™ ligand (see for example U.S. Patent Publication No. 2009/0136465). Thus, the ZFP may be operably linked to the regulatable functional domain wherein the resultant activity of the ZFP-TF is controlled by the external ligand.

Nucleases

In certain embodiments, described herein are artificial nucleases comprising a DNA-binding binding domain and cleavage (nuclease) domain. As such, gene modification can be achieved using a nuclease, for example an engineered nuclease. Engineered nuclease technology is based on the engineering of naturally occurring DNA-binding proteins. For example, engineering of homing endonucleases with tailored DNA-binding specificities has been described. Chames et al. (2005) *Nucleic Acids Res* 33(20):e178; Arnould et al. (2006) *J. Mol. Biol.* 355:443-458. In addition, engineering of ZFPs has also been described. See, e.g., U.S. Pat. Nos. 6,534,261; 6,607,882; 6,824,978; 6,979,539; 6,933,113; 7,163,824; and 7,013,219.

In addition, ZFPs and/or TALEs have been fused to nuclease domains to create ZFNs and TALENs—a functional entity that is able to recognize its intended nucleic acid target through its engineered (ZFP or TALE) DNA binding domain and cause the DNA to be cut near the DNA binding site via the nuclease activity. See, e.g., Kim et al. (1996) *Proc Nat'l Acad Sci USA* 93(3):1156-1160. More recently, such nucleases have been used for genome modification in a variety of organisms. See, for example, U.S. Patent Publication Nos. 2003/0232410; 2005/0208489; 2005/0026157; 2005/0064474; 2006/0188987; 2006/0063231; and International Patent Publication No. WO 07/014275.

Thus, the methods and compositions described herein are broadly applicable and may involve any nuclease of interest. Non-limiting examples of nucleases include meganucleases, TALENs and zinc finger nucleases. The nuclease may comprise heterologous DNA-binding and cleavage domains (e.g., zinc finger nucleases; meganuclease DNA-binding domains with heterologous cleavage domains) or, alternatively, the DNA-binding domain of a naturally-occurring nuclease may be altered to bind to a selected target site (e.g., a meganuclease that has been engineered to bind to site different than the cognate binding site).

In any of the nucleases described herein, the nuclease can comprise an engineered TALE DNA-binding domain and a nuclease domain (e.g., endonuclease and/or meganuclease domain), also referred to as TALENs. Methods and compositions for engineering these TALEN proteins for robust, site specific interaction with the target sequence of the user's choosing have been published (see U.S. Pat. No. 8,586,526). In some embodiments, the TALEN comprises an endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel et al. (2013) *Nucl Acid Res.* 42(4): 2591-601, doi: 10.1093/nar/gkt1224). In addition, the nuclease domain may also exhibit DNA-binding functionality.

In still further embodiments, the nuclease comprises a compact TALEN (cTALEN). These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley et al. (2013) *Nat Comm* 4:1762, doi: 10.1038/ncomms2782). Any TALENs may be used in combination with additional TALENs (e.g., one or more TALENs (cTALENs or FokI-TALENs) with one or more mega-TALs) or other DNA cleavage enzymes.

In certain embodiments, the nuclease comprises a meganuclease (homing endonuclease) or a portion thereof that exhibits cleavage activity. Naturally-occurring meganucleases recognize 15-40 base-pair cleavage sites and are commonly grouped into four families: the LAGLIDADG family (SEQ ID NO: 29), the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22:1125-1127; Jasin (1996) *Trends Genet.* 12:224-228; Gimble et al. (1996)*J Mol. Biol.* 263:163-180; Argast et al. (1998)*J Mol. Biol.* 280:345-353 and the New England Biolabs catalogue.

DNA-binding domains from naturally-occurring meganucleases, primarily from the LAGLIDADG family (SEQ ID NO: 29), have been used to promote site-specific genome modification in plants, yeast, *Drosophila*, mammalian cells and mice, but this approach has been limited to the modification of either homologous genes that conserve the meganuclease recognition sequence (Monet et al. (1999) *Biochem. Biophysics. Res. Common.* 255:88-93) or to preengineered genomes into which a recognition sequence has been introduced (Route et al. (1994) *Mol. Cell. Biol.* 14:8096-106; Chilton et al. (2003) *Plant Physiology.* 133:956-65; Puchta et al. (1996) *Proc. Natl. Acad. Sci. USA* 93:5055-60; Rong et al. (2002) *Genes Dev.* 16:1568-81; Gouble et al. (2006) *J. Gene Med.* 8(5):616-622). Accordingly, attempts have been made to engineer meganucleases to exhibit novel binding specificity at medically or biotechnologically relevant sites (Porteus et al. (2005) *Nat. Biotechnol.* 23:967-73; Sussman et al. (2004) *J. Mol. Biol.* 342:31-41; Epinat et al. (2003) *Nucleic Acids Res.* 31:2952-62; Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication Nos. 2007/0117128; 2006/0206949; 2006/0153826; 2006/0078552; and 2004/0002092). In addition, naturally-occurring or engineered DNA-binding domains from meganucleases can be operably linked with a cleavage domain from a heterologous nuclease (e.g., FokI) and/or cleavage domains from meganucleases can be operably linked with a heterologous DNA-binding domain (e.g., ZFP or TALE).

In other embodiments, the nuclease is a zinc finger nuclease (ZFN) or TALE DNA binding domain-nuclease fusion (TALEN). ZFNs and TALENs comprise a DNA binding domain (zinc finger protein or TALE DNA binding domain) that has been engineered to bind to a target site in a gene of choice and cleavage domain or a cleavage half-domain (e.g., from a restriction and/or meganuclease as described herein).

As described in detail above, zinc finger binding domains and TALE DNA binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain or TALE protein can have a novel binding specificity, compared to a naturally-occurring protein. Engineering methods include, but are not limited to, rational design and various types of selection. Rational design includes, for example, using databases comprising triplet (or quadruplet) nucleotide sequences and individual zinc finger or TALE amino acid sequences, in which each triplet or quadruplet nucleotide sequence is associated with one or more amino acid sequences of zinc fingers or TALE repeat units which bind the particular triplet or quadruplet sequence. See, for example, U.S. Pat. Nos. 6,453,242 and 6,534,261, incorporated by reference herein in their entireties.

Selection of target sites; and methods for design and construction of fusion molecules (and polynucleotides encoding same) are known to those of skill in the art and described in detail in U.S. Pat. Nos. 7,888,121 and 8,409,861, incorporated by reference in their entireties herein. In certain embodiments, the target site of the DNA-binding domain of the fusion molecules described herein (nucleases, transcription factors, etc.) in in intron 1 of a CFTR gene, for example a target site comprising 9, 10, 11, 12, 13, 14, 15, 16, 17, 18 or more nucleotides of the target sequences shown in Table 2; International Patent Publication No. 2018/204469 or U.S. Pat. No. 9,161,995.

In addition, as disclosed in these and other references, zinc finger domains, TALEs and/or multi-fingered zinc finger proteins may be linked together using any suitable linker sequences, including for example, linkers of 5 or more amino acids in length (e.g., TGEKP (SEQ ID NO:1), TGGQRP (SEQ ID NO:2), TGQKP (SEQ ID NO:3), and/or TGSQKP (SEQ ID NO:4). See, e.g., U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. See, also, U.S. Pat. No. 8,772,453.

Thus, nucleases such as ZFNs, TALENs and/or meganucleases can comprise any DNA-binding domain and any nuclease (cleavage) domain (cleavage domain, cleavage half-domain). As noted above, the cleavage domain may be heterologous to the DNA-binding domain, for example a zinc finger or TAL-effector DNA-binding domain and a cleavage domain from a nuclease or a meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., 51 Nuclease; mung bean nuclease; pancreatic DNase I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion molecules are required for cleavage if the fusion molecules comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion molecules are preferably disposed, with respect to each other, such that binding of the two fusion molecules to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites, but may lie 1 or more kilobases away from the cleavage site, including between 1-50 base pairs (or any value therebetween), 1-100 base pairs (or any value therebetween), 100-500 base pairs (or any value therebetween), 500 to 1000 base pairs (or any value therebetween) or even more than 1 kb from the cleavage site.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150; and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31,978-31,982. Thus, in one embodiment, fusion molecules comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is FokI. This particular enzyme is active as a dimer. Bitinaite et al. (1998) Proc. Natl. Acad. Sci. USA 95:10,570-10,575. Accordingly, for the purposes of the present disclosure, the portion of the FokI enzyme used in the disclosed fusion molecules is considered a cleavage half-domain. Thus, for targeted double-stranded cleavage and/or targeted replacement of cellular sequences using zinc finger-FokI fusions, two fusion molecules, each comprising a FokI cleavage half-domain, can be used to reconstitute a catalytically active cleavage domain. Alternatively, a single polypeptide molecule containing a zinc finger binding domain and two FokI cleavage half-domains can also be used. Parameters for targeted cleavage and targeted sequence alteration using zinc finger-FokI fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Patent Publication No. WO 07/014275, incorporated herein in its entirety. Additional restriction enzymes also contain separable binding and cleavage domains, and these are contemplated by the present disclosure. See, for example, Roberts et al. (2003) Nucleic Acids Res. 31:418-420.

In certain embodiments, the cleavage domain comprises a FokI cleavage domain used to generate the crystal structures 1FOK.pdb and 2FOK.pdb (see Wah et al. (1997) Nature 388:97-100) having the sequence shown below:

Wild type FokI cleavage half domain
(SEQ ID NO: 5)
QLVKSELEEKKSELRHKLKYVPHEYIELIEIARNSTQDRILEMKVMEF

FMKVYGYRGKHLGGSRKPDGAIYTVGSPIDYGVIVDTKAYSGGYNLPI

GQADEMQRYVEENQTRNKHINPNEWWKVYPSSVTEFKFLFVSGHFKGN

YKAQLTRLNHITNCNGAVLSVEELLIGGEMIKAGTLTLEEVRRKFNNG

EINF

Cleavage half domains derived from FokI may comprise a mutation in one or more of amino acid residues as shown in SEQ ID NO:5. Mutations include substitutions (of a wild-type amino acid residue for a different residue, insertions (of one or more amino acid residues) and/or deletions (of one or more amino acid residues). In certain embodiments, one or more of residues 414-426, 443-450, 467-488, 501-502, and/or 521-531 (numbered relative to SEQ ID NO:40) are mutated since these residues are located close to the DNA backbone in a molecular model of a ZFN bound to its target site described in Miller et al. ((2007) Nat Biotechnol 25:778-784). In certain embodiments, one or more residues at positions 416, 422, 447, 448, and/or 525 are mutated. In certain embodiments, the mutation comprises a substitution of a wild-type residue with a different residue, for example a serine (S) residue. See, e.g., U.S. Patent Publication No. 2018/0087072.

In certain embodiments, the cleavage domain comprises one or more engineered cleavage half-domain (also referred to as dimerization domain mutants) that minimize or prevent homodimerization, as described, for example, in U.S. Pat. Nos. 7,914,796; 8,034,598; and 8,623,618; and U.S. Patent Publication No. 2011/0201055, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI (numbered relative to SEQ ID NO:5) are all targets for influencing dimerization of the FokI cleavage half-domains. The mutations may include mutations to residues found in natural restriction enzymes homologous to FokI. In a preferred embodiment, the mutation at positions 416, 422, 447, 448 and/or 525 (numbered relative to SEQ ID NO:5) comprise replacement of a positively charged amino acid with an uncharged or a negatively charged amino acid. In another embodiment, the engineered cleavage half domain comprises mutations in amino acid residues 499, 496 and 486 in addition to the mutations in one or more amino acid residues 416, 422, 447, 448, or 525, all numbered relative to wild-type (SEQ ID NO:5).

In certain embodiments, the compositions described herein include engineered cleavage half-domains of FokI that form obligate heterodimers as described, for example, in U.S. Pat. Nos. 7,914,796; 8,034,598; 8,961,281; and 8,623,618; U.S. Patent Publication Nos. 2008/0131962 and 2012/0040398. Thus, in one preferred embodiment, the invention provides fusion molecules wherein the engineered cleavage half-domain comprises a polypeptide in which the wild-type Gln (Q) residue at position 486 is replaced with a Glu (E) residue, the wild-type Ile (I) residue at position 499 is replaced with a Leu (L) residue and the wild-type Asn (N) residue at position 496 is replaced with an Asp (D) or a Glu (E) residue ("ELD" or "ELE") in addition to one or more mutations at positions 416, 422, 447, 448, or 525 (numbered relative to wild-type (SEQ ID NO:5)). In another embodiment, the engineered cleavage half domains are derived from a wild-type FokI cleavage half domain and comprise mutations in the amino acid residues 490, 538 and 537, numbered relative to wild-type FokI (SEQ ID NO:5) in addition to the one or more mutations at amino acid residues 416, 422, 447, 448, or 525. In a preferred embodiment, the invention provides a fusion molecules, wherein the engineered cleavage half-domain comprises a polypeptide in which the wild-type Glu (E) residue at position 490 is replaced with a Lys (K) residue, the wild-type Ile (I) residue at position 538 is replaced with a Lys (K) residue, and the wild-type His (H) residue at position 537 is replaced with a Lys (K) residue or an Arg (R) residue ("KKK" or "KKR") (see U.S. Pat. No. 8,962,281, incorporated by reference herein) in addition to one or more mutations at positions 416, 422, 447, 448, or 525. See, e.g., U.S. Pat. Nos. 7,914,796; 8,034,598; and 8,623,618, the disclosures of which are incorporated by reference in its entirety for all purposes. In other embodiments, the engineered cleavage half domain comprises the "Sharkey" and/or some of the "Sharkey" mutations (see Guo et al. (2010)J. Mol. Biol. 400(1):96-107).

In another embodiment, the engineered cleavage half domains are derived from a wild-type FokI cleavage half domain and comprise mutations in the amino acid residues 490, and 538, numbered relative to wild-type FokI in addition to the one or more mutations at amino acid residues 416, 422, 447, 448, or 525. In a preferred embodiment, the invention provides a fusion molecule, wherein the engineered cleavage half-domain comprises a polypeptide in which the wild-type Glu (E) residue at position 490 is replaced with a Lys (K) residue, and the wild-type Ile (I) residue at position 538 is replaced with a Lys (K) residue ("KK") in addition to one or more mutations at positions 416, 422, 447, 448, or 525. In a preferred embodiment, the invention provides a fusion molecule, wherein the engineered cleavage half-domain comprises a polypeptide in which the wild-type Gln (Q) residue at position 486 is replaced with an Glu (E) residue, and the wild-type Ile (I) residue at position 499 is replaced with a Leu (L) residue ("EL") (See U.S. Pat. No. 8,034,598, incorporated by reference herein) in addition to one or more mutations at positions 416, 422, 447, 448, or 525.

In one aspect, the invention provides a fusion molecule wherein the engineered cleavage half-domain comprises a polypeptide in which the wild-type amino acid residue at one or more of positions 387, 393, 394, 398, 400, 402, 416, 422, 427, 434, 439, 441, 447, 448, 469, 487, 495, 497, 506, 516, 525, 529, 534, 559, 569, 570, 571 in the FokI catalytic domain are mutated. In some embodiments, these mutations in the FokI domain prevent or lessen non-specific interactions between the FokI domain and the phosphate contained in a DNA backbone. In some embodiments, the one or more mutations alter the wild type amino acid from a positively charged residue to a neutral residue or a negatively charged residue. In any of these embodiments, the mutants described may also be made in a FokI domain comprising one or more additional mutations. In preferred embodiments, these additional mutations are in the dimerization domain, e.g. at positions 499, 496, 486, 490, 538 and 537.

Alternatively, nucleases may be assembled in vivo at the nucleic acid target site using so-called "split-enzyme" technology (see e.g. U.S. Patent Publication No. 2009/0068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases (e.g., ZFNs and/or TALENs) can be screened for activity prior to use, for example in a yeast-based chromosomal system as described in as described in U.S. Pat. No. 8,563,314.

In certain embodiments, the nuclease comprises a CRISPR/Cas system. The CRISPR (clustered regularly interspaced short palindromic repeats) locus, which encodes RNA components of the system, and the Cas (CRISPR-associated) locus, which encodes proteins (Jansen et al. (2002) *Mol. Microbiol.* 43:1565-1575; Makarova et al. (2002) *Nucleic Acids Res.* 30:482-496; Makarova et al. (2006) *Biol. Direct* 1:7; Haft et al. (2005) *PLoS Comput. Biol.* 1:e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In some embodiments, the CRISPR-Cpf1 system is used. The CRISPR-Cpf1 system, identified in *Francisella* spp, is a class 2 CRISPR-Cas system that mediates robust DNA interference in human cells. Although functionally conserved, Cpf1 and Cas9 differ in many aspects including in their guide RNAs and substrate specificity (see Fagerlund et al. (2015) *Genom Bio* 16:251). A major difference between Cas9 and Cpf1 proteins is that Cpf1 does not utilize tracrRNA, and thus requires only a crRNA. The FnCpf1 crRNAs are 42-44 nucleotides long (19-nucleotide repeat and 23-25-nucleotide spacer) and contain a single stem-loop, which tolerates sequence changes that retain secondary structure. In addition, the Cpf1 crRNAs are significantly shorter than the ~100-nucleotide engineered sgRNAs required by Cas9, and the PAM requirements for FnCpf1 are 5'-TTN-3' and 5'-CTA-3' on the displaced strand. Although both Cas9 and Cpf1 make double strand breaks in the target DNA, Cas9 uses its RuvC- and HNH-like domains to make blunt-ended cuts within the seed sequence of the guide RNA, whereas Cpf1 uses a RuvC-like domain to produce staggered cuts outside of the seed. Because Cpf1 makes staggered cuts away from the critical seed region, NHEJ will not disrupt the target site, therefore ensuring that Cpf1 can continue to cut the same site until the desired HDR recombination event has taken place. Thus, in the methods and compositions described herein, it is understood that the term "Cas" includes both Cas9 and Cfp1 proteins. Thus, as used herein, a "CRISPR/Cas system" refers both CRISPR/Cas and/or CRISPR/Cfp1 systems, including both nuclease(s), nickase and/or transcription factor systems.

In some embodiments, other Cas proteins may be used. Some exemplary Cas proteins include Cas9, Cpf1 (also known as Cas12a), C2c1, C2c2 (also known as Cas13a), C2c3, Cas1, Cas2, Cas4, CasX and CasY; and include engineered and natural variants thereof (Burstein et al. (2017) *Nature* 542:237-241) for example HF1/spCas9 (Kleinstiver et al. (2016) *Nature* 529:490-495; Cebrian-Serrano and Davies (2017) *Mamm Genome* 28(7):247-261); split Cas9 systems (Zetsche et al. (2015) *Nat Biotechnol* 33(2):139-142), trans-spliced Cas9 based on an intein-extein system (Troung et al. (2015) *Nucl Acid Res* 43(13):6450-8); mini-SaCas9 (Ma et al. (2018) *ACS Synth Biol* 7(4):978-985). Thus, in the methods and compositions described herein, it is understood that the term "Cas" includes all Cas variant proteins, both natural and engineered.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof such as derivative Cas proteins. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein. In some embodiments, the Cas protein is a small Cas9 ortholog for delivery via an AAV vector (Ran et al. (2015) Nature 510:186).

The nuclease(s) may make one or more double-stranded and/or single-stranded cuts in the target site. In certain embodiments, the nuclease comprises a catalytically inactive cleavage domain (e.g., FokI and/or Cas protein). See, e.g., U.S. Pat. Nos. 9,200,266; 8,703,489 and Guillinger et al. (2014) Nature Biotech. 32(6):577-582. The catalytically inactive cleavage domain may, in combination with a catalytically active domain act as a nickase to make a single-stranded cut. Therefore, two nickases can be used in combination to make a double-stranded cut in a specific region. Additional nickases are also known in the art, for example, McCaffery et al. (2016) Nucleic Acids Res. 44(2):e11. doi: 10.1093/nar/gkv878. Epub 2015 Oct 19.

Compounds

In an aspect, the invention includes LNPs comprising cationic lipid compounds which are capable of combining with other lipid components such as neutral lipids, charged lipids, steroids and/or polymer conjugated-lipids to form lipid nanoparticles with oligonucleotides. Without wishing to be bound by theory, it is thought that these lipid nanoparticles shield oligonucleotides from degradation in the serum and provide for effective delivery of oligonucleotides to cells in vitro and in vivo.

In one embodiment, the LNPs comprise a polynucleotide having activity as a gene therapy reagent and a lipid compound having the structure of shown in U.S. Patent Publication No. 2019/0060482, and hereby explicitly incorporated by reference in its entirety as though fully set forth herein. In certain embodiments, the LNP comprises:
(i) a first cationic lipid at a compositional molar ratio from about 0.18 to about 0.32 and of formula:

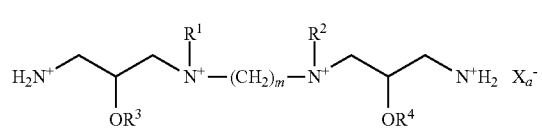

(I)

wherein $R^1$ and $R^2$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ and $R^4$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; m is an integer from 1 to 6; $X_a^-$ is an anion;
(ii) a second cationic lipid at a compositional molar ratio from about 0.24 to about 0.51 and of formula:

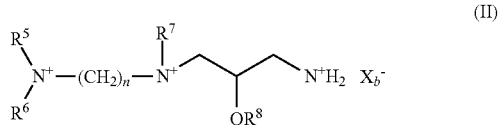

(II)

wherein $R^5$ and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^6$ and $R^7$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; n is an integer from 1 to 6; and $X_b^-$ is an anion;
(iii) a first helper lipid at a compositional molar ratio from about 0.20 to about 0.32;
(iv) a second helper lipid at a compositional molar ratio from about 0.01 to about 0.14; and
(v) a biostability enhancing agent at a compositional molar ratio from about 0.01 to about 0.02.

Delivery

For the purposes of administration, the LNPs of the present invention may be administered as a raw chemical or may be formulated as pharmaceutical compositions. Pharmaceutical compositions of the present invention comprise an LNP comprising a therapeutic agent, such as a polynucleotide having activity as a gene therapy reagent, and one or more pharmaceutically acceptable carrier, diluent or excipient. The LNP is present in the composition in an amount which is effective to form a lipid nanoparticle and deliver the therapeutic agent, e.g., for treating a particular disease or condition of interest. Appropriate concentrations and dosages can be readily determined by one skilled in the art.

The proteins (e.g., nucleases), polynucleotides and/or compositions comprising the proteins and/or polynucleotides described herein may be delivered to a target cell by any suitable means, including, for example, by injection of an LNP comprising the protein and/or mRNA components.

Suitable cells include but are not limited to eukaryotic and prokaryotic cells and/or cell lines. Non-limiting examples of such cells or cell lines generated from such cells include T-cells, COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as Spodoptera fugiperda (Sf), or fungal cells such as Saccharomyces, Pichia and Schizosaccharomyces. In certain embodiments, the cell line is a CHO-K1, MDCK or HEK293 cell line. Suitable cells also include stem cells such as, by way of example, embryonic stem cells, induced pluripotent stem cells (iPS cells), hematopoietic stem cells, neuronal stem cells and mesenchymal stem cells.

Methods of delivering proteins comprising DNA-binding domains also include those described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

DNA binding domains and fusion molecules comprising these DNA binding domains as described herein may also be delivered using vectors containing sequences encoding one or more of the DNA-binding protein(s). Additionally, additional nucleic acids (e.g., donors) also may be delivered via these vectors. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more DNA-binding protein-encoding sequences and/or additional nucleic acids as appropriate. Thus, when one or more DNA-binding proteins as described herein are introduced into the cell, and additional DNAs as appropriate, they may be carried on the same vector or on different vectors. When multiple vectors are used, each vector may comprise a sequence encoding one or multiple DNA-binding proteins and additional nucleic acids as desired.

Conventional viral and non-viral based gene transfer methods can be used to introduce nucleic acids encoding engineered DNA-binding proteins in cells (e.g., mammalian cells) and target tissues and to co-introduce additional nucleotide sequences as desired. Such methods can also be used to administer nucleic acids (e.g., encoding DNA-binding proteins and/or donors) to cells in vitro. In certain embodiments, nucleic acids are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson (1992) *Science* 256:808-813; Nabel & Felgner (1993) *TIBTECH* 11:211-217; Mitani & Caskey (1993) *TIBTECH* 11:162-166 (1993); Dillon (1993) *TIBTECH* 11:167-175; Miller (1992) *Nature* 357: 455-460; Van Brunt (1988) *Biotechnology* 6(10):1149-1154; Vigne (1995) *Restorative Neurology and Neuroscience* 8:35-36; Kremer & Perricaudet (1995) *British Medical Bulletin* 51(1):31-44; Haddada et al. in *Current Topics in Microbiology and Immunology* Doerfler and Bohm (eds.) (1995); and Yu et al. (1994) *Gene Therapy* 1:13-26.

Methods of non-viral delivery of nucleic acids include electroporation, lipofection, microinjection, biolistics, virosomes, liposomes, lipid nanoparticles, immunoliposomes, polycation or lipid:nucleic acid conjugates, naked DNA, mRNA, artificial virions, and agent-enhanced uptake of DNA. Sonoporation using, e.g., the Sonitron 2000 system (Rich-Mar) can also be used for delivery of nucleic acids. In a preferred embodiment, one or more nucleic acids are delivered as mRNA. Also preferred is the use of capped mRNAs to increase translational efficiency and/or mRNA stability. Especially preferred are ARCA (anti-reverse cap analog) caps or variants thereof. See U.S. Pat. Nos. 7,074,596 and 8,153,773, incorporated by reference herein.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™, Lipofectin™, and Lipofectamine™ RNAiMAX). Cationic and neutral lipids that are suitable for efficient receptor-recognition lipofection of polynucleotides include those of Felgner, International Patent Publication Nos. WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal (1995) *Science* 270:404-410; Blaese et al. (1995) *Cancer Gene Ther.* 2:291-297; Behr et al. (1994) *Bioconjugate Chem.* 5:382-389; Remy et al. (1994) *Bioconjugate Chem.* 5:647-654; Gao et al. (1995) *Gene Therapy* 2:710-722; Ahmad et al. (1992) *Cancer Res.* 52:4817-4820; U.S. Pat. Nos. 4,186, 183; 4,217,344; 4,235,871; 4,261,975; 4,485,054; 4,501, 728; 4,774,085; 4,837,028; and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al. (2009) *Nature Biotechnology* 27(7):643).

The use of RNA or DNA viral based systems for the delivery of nucleic acids encoding engineered DNA-binding proteins, and/or donors as desired takes advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al. (1992) *J. Virol.* 66:2731-2739; Johann et al. (1992) *J. Virol.* 66:1635-1640; Sommerfelt et al. (1990) *Virol.* 176:58-59; Wilson et al. (1989) *J. Virol.* 63:2374-2378; Miller et al. (1991) *J. Virol.* 65:2220-2224; International Patent Publication No. WO 94/26877).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al. (1987) *Virology* 160:38-47; U.S. Pat. No. 4,797,368; International Patent Publication No. WO 93/24641; Kotin (1994) *Human Gene Therapy* 5:793-801; Muzyczka (1994) 1 *Clin. Invest.* 94:1351. Construction of recombinant AAV vectors are described in a number of publications, including U.S. Pat. No. 5,173,414; Tratschin et al. (1985) *Mol. Cell. Biol.* 5:3251-3260; Tratschin et al. (1984) *Mol. Cell. Biol.* 4:2072-2081; Hermonat & Muzyczka (1984) *PNAS USA* 81:6466-6470; and Samulski et al. (1989) *J. Virol.* 63:03822-3828.

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al. (1995) *Blood* 85:3048-305; Kohn et al. (1995) *Nat. Med.* 1:1017-102; Malech et al. (1997) *PNAS USA* 94(22):12133-12138). PA317/pLASN was the first therapeutic vector used in a gene therapy trial. (Blaese et al. (1995) *Science* 270:475-480). Transduction efficiencies of 50% or greater have been observed for MFG-S packaged vectors. (Ellem et al. (1997) *Immunol Immunother.* 44(1):10-20; Dranoff et al. (1997) *Hum. Gene Ther.* 1:111-2.

Recombinant adeno-associated virus vectors (rAAV) are a promising alternative gene delivery system based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al. (1998) *Lancet* 351(9117):1702-3; Kearns et al. (1996) *Gene Ther.* 9:748-55). Other AAV serotypes, including AAV1, AAV3, AAV4, AAV5, AAV6, AAV8, AAV8.2, AAV9 and AAVrh10 and pseudotyped AAV such as AAV2/8, AAV2/5 and AAV2/6 can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al. (1998) *Hum. Gene Ther.* 7:1083-9). Additional examples of the use of adenovirus vectors for gene transfer in clinical trials include Rosenecker et al. (1996) *Infection* 24(1):5-10; Sterman et al. (1998) *Hum. Gene Ther.* 9(7):1083-1089; Welsh et al. (1995) *Hum. Gene Ther.* 2:205-18; Alvarez et al. (1997) *Hum. Gene Ther.* 5:597-613; Topf et al. (1998) *Gene Ther.* 5:507-513; Sterman et al. (1998) *Hum. Gene Ther.* 7:1083-1089.

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. In addition, AAV can be manufactured using a baculovirus system (see e.g. U.S. Pat. Nos. 6,723,551 and 7,271,002).

Purification of AAV particles from a 293 or baculovirus system typically involves growth of the cells which produce the virus, followed by collection of the viral particles from the cell supernatant or lysing the cells and collecting the virus from the crude lysate. AAV is then purified by methods known in the art including ion exchange chromatography (e.g. see U.S. Pat. Nos. 7,419,817 and 6,989,264), ion exchange chromatography and CsCl density centrifugation (e.g. International Patent Publication No. WO 2011/094198 A10), immunoaffinity chromatography (e.g. International Patent Publication No. WO 2016/128408) or purification using AVB Sepharose (e.g. GE Healthcare Life Sciences).

In many gene therapy applications, it is desirable that the gene therapy vector be delivered with a high degree of specificity to a particular tissue type. Accordingly, a viral vector can be modified to have specificity for a given cell type by expressing a ligand as a fusion molecule with a viral coat protein on the outer surface of the virus. The ligand is chosen to have affinity for a receptor known to be present on the cell type of interest. For example, Han et al. (1995) *Proc. Natl. Acad. Sci. USA* 92:9747-9751), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion molecule comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Delivery methods for CRISPR/Cas systems can comprise those methods described above. For example, in animal models, in vitro transcribed Cas encoding mRNA or recombinant Cas protein can be directly injected into one-cell stage embryos using glass needles to genome-edited animals. To express Cas and guide RNAs in cells in vitro, typically plasmids that encode them are transfected into cells via lipofection or electroporation. Also, recombinant Cas protein can be complexed with in vitro transcribed guide RNA where the Cas-guide RNA ribonucleoprotein is taken up by the cells of interest (Kim et al. (2014) *Genome Res* 24(6):1012). For therapeutic purposes, Cas and guide RNAs can be delivered by a combination of viral and non-viral techniques. For example, mRNA encoding Cas may be delivered via nanoparticle delivery while the guide RNAs and any desired transgene or repair template are delivered via AAV (Yin et al. (2016) *Nat Biotechnol* 34(3):328).

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by re-implantation of the cells into a patient, usually after selection for cells which have incorporated the vector.

Ex vivo cell transfection for diagnostics, research, transplant or for gene therapy (e.g., via re-infusion of the transfected cells into the host organism) is well known to those of skill in the art. In a preferred embodiment, cells are isolated from the subject organism, transfected with a DNA-binding proteins nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients.

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al. (1992) *J. Exp. Med.* 176:1693-1702).

Stem cells are isolated for transduction and differentiation using known methods. For example, stem cells are isolated from bone marrow cells by panning the bone marrow cells with antibodies which bind unwanted cells, such as CD4+ and CD8+(T cells), CD45+(panB cells), GR-1 (granulocytes), and Tad (differentiated antigen presenting cells) (see Inaba et al. (1992) *J. Exp. Med.* 176:1693-1702).

Stem cells that have been modified may also be used in some embodiments. For example, neuronal stem cells that have been made resistant to apoptosis may be used as therapeutic compositions where the stem cells also contain the ZFP TFs of the invention. Resistance to apoptosis may come about, for example, by knocking out BAX and/or BAK using BAX- or BAK-specific ZFNs (see U.S. Pat. No. 8,597,912) in the stem cells, or those that are disrupted in a caspase, again using caspase-6 specific ZFNs for example.

Vectors (e.g., retroviruses, adenoviruses, liposomes, etc.) containing therapeutic DNA-binding proteins (or nucleic acids encoding these proteins) can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34+ cells, include adenovirus Type 35.

Vectors suitable for introduction of transgenes into immune cells (e.g., T-cells) include non-integrating lentivirus vectors. See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222.

As noted above, the disclosed methods and compositions can be used in any type of cell including, but not limited to, prokaryotic cells, fungal cells, Archaeal cells, plant cells, insect cells, animal cells, vertebrate cells, mammalian cells and human cells, including T-cells and stem cells of any type. Suitable cell lines for protein expression are known to those of skill in the art and include, but are not limited to COS, CHO (e.g., CHO-S, CHO-K1, CHO-DG44, CHO-DUXB11), VERO, MDCK, WI38, V79, B14AF28-G3, BHK, HaK, NS0, SP2/0-Ag14, HeLa, HEK293 (e.g., HEK293-F, HEK293-H, HEK293-T), perC6, insect cells such as *Spodoptera* fugiperda (Sf), and fungal cells such as *Saccharomyces*, *Pichia* and *Schizosaccharomyces*. Progeny, variants and derivatives of these cell lines can also be used.

Compositions

Pharmaceutically acceptable carriers are determined in part by the particular composition being administered, as well as by the particular method used to administer the composition.

Administration of the compositions of the invention can be carried out via any of the accepted modes of administration of agents for serving similar utilities. The pharmaceutical compositions of the invention may be formulated into preparations in solid, semi solid, liquid or gaseous forms, such as tablets, capsules, powders, granules, ointments, solutions, suspensions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intradermal, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy*, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi solid, semi liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose; agents to act as cryoprotectants such as sucrose or trehalose. The parenteral preparation can be enclosed in ampoules, disposable syringes or multiple dosevials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, or a protein.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi phasic, or tri phasic systems in order to deliver the active ingredient(s). Delivery of the aerosol includes the necessary container, activators, valves, sub-containers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining the lipid nanoparticles of the invention with sterile, distilled water or other carrier so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compositions of the invention, or their pharmaceutically acceptable salts, are administered in a therapeutically effective amount, which will vary depending upon a variety of factors including the activity of the specific therapeutic agent employed; the metabolic stability and length of action of the therapeutic agent; the age, body weight, general health, sex, and diet of the patient; the mode and time of administration; the rate of excretion; the drug combination; the severity of the particular disorder or condition; and the subject undergoing therapy.

Compositions of the invention may also be administered simultaneously with, prior to, or after administration of one or more other therapeutic agents. Such combination therapy includes administration of a single pharmaceutical dosage formulation of a composition of the invention and one or more additional active agents, as well as administration of the composition of the invention and each active agent in its own separate pharmaceutical dosage formulation. For example, a composition of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

Preparation methods for the above compounds and compositions are described herein below and/or known in the art.

It will be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include C(O) R" (where R" is alkyl, aryl or arylalkyl), p methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, (1999), *Protective Groups in Organic Synthesis,* 3rd Ed., Wiley. As one of skill in the art would appreciate, the protecting group may also be a polymer resin such as a Wang resin, Rink resin or a 2-chlorotrityl-chloride resin.

Furthermore, all lipids which exist in free base or acid form can be converted to their pharmaceutically acceptable salts by treatment with the appropriate inorganic or organic base or acid by methods known to one skilled in the art. Salts of the lipids can be converted to their free base or acid form by standard techniques.

Applications

Use of engineered gene therapy in treatment and prevention of disease is expected to be one of the most significant developments in medicine in the coming years. The methods and compositions described herein serve to increase the specificity of these novel tools to ensure that the desired target sites will be the primary place of cleavage. Minimizing or eliminating off-target cleavage will be required to realize the full potential of this technology, for all in vitro, in vivo and ex vivo applications.

Exemplary genetic diseases include, but are not limited to, achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the $6^{th}$ codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, porphyria, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

Additional exemplary diseases that can be treated by targeted DNA cleavage and/or homologous recombination include acquired immunodeficiencies, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

Such methods also allow for treatment of infections (viral or bacterial) in a host (e.g., by blocking expression of viral or bacterial receptors, thereby preventing infection and/or spread in a host organism) to treat genetic diseases.

Targeted cleavage of infecting or integrated viral genomes can be used to treat viral infections in a host. Additionally, targeted cleavage of genes encoding receptors for viruses can be used to block expression of such receptors, thereby preventing viral infection and/or viral spread in a host organism. Targeted mutagenesis of genes encoding viral receptors (e.g., the CCR5 and CXCR4 receptors for HIV) can be used to render the receptors unable to bind to virus, thereby preventing new infection and blocking the spread of existing infections. See, U.S. Patent Publication No. 2008/015996. Non-limiting examples of viruses or viral receptors that may be targeted include herpes simplex virus (HSV), such as HSV-1 and HSV-2, varicella zoster virus (VZV), Epstein-Barr virus (EBV) and cytomegalovirus (CMV), HHV6 and HHV7. The hepatitis family of viruses includes hepatitis A virus (HAV), hepatitis B virus (HBV), hepatitis C virus (HCV), the delta hepatitis virus (HDV), hepatitis E virus (HEV) and hepatitis G virus (HGV). Other viruses or their receptors may be targeted, including, but not limited to, Picornaviridae (e.g., polioviruses, etc.); Caliciviridae; Togaviridae (e.g., rubella virus, dengue virus, etc.); Flaviviridae;

Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae; lentiviruses (e.g., HTLV-I; HTLV-II; HIV-1 (also known as HTLV-III, LAV, ARV, hTLR, etc.) HIV-II); simian immunodeficiency virus (SIV), human papillomavirus (HPV), influenza virus and the tick-borne encephalitis viruses. See, e.g. Virology, 3rd Edition (W. K. Joklik ed. 1988); Fundamental Virology, 2nd Edition (B. N. Fields and D. M. Knipe, eds. 1991), for a description of these and other viruses. Receptors for HIV, for example, include CCR-5 and CXCR-4.

As noted above, the compositions and methods described herein can be used for gene modification, gene correction, and gene disruption. Non-limiting examples of gene modification includes homology directed repair (HDR)-based targeted integration; HDR-based gene correction; HDR-based gene modification; HDR-based gene disruption; NHEJ-based gene disruption and/or combinations of HDR, NHEJ, and/or single strand annealing (SSA). Single-Strand Annealing (SSA) refers to the repair of a double strand break between two repeated sequences that occur in the same orientation by resection of the DSB by 5'-3' exonucleases to expose the 2 complementary regions. The single-strands encoding the 2 direct repeats then anneal to each other, and the annealed intermediate can be processed such that the single-stranded tails (the portion of the single-stranded DNA that is not annealed to any sequence) are be digested away, the gaps filled in by DNA Polymerase, and the DNA ends rejoined. This results in the deletion of sequences located between the direct repeats.

Compositions comprising cleavage domains (e.g., ZFNs, TALENs, CRISPR/Cas systems) and methods described herein can also be used in the treatment of various genetic diseases and/or infectious diseases.

The compositions and methods can also be applied to stem cell based therapies, including but not limited to: correction of somatic cell mutations by short patch gene conversion or targeted integration for monogenic gene therapy; disruption of dominant negative alleles; disruption of genes required for the entry or productive infection of pathogens into cells; enhanced tissue engineering, for example, by modifying gene activity to promote the differentiation or formation of functional tissues; and/or disrupting gene activity to promote the differentiation or formation of functional tissues; blocking or inducing differentiation, for example, by disrupting genes that block differentiation to promote stem cells to differentiate down a specific lineage pathway, targeted insertion of a gene or siRNA expression cassette that can stimulate stem cell differentiation, targeted insertion of a gene or siRNA expression cassette that can block stem cell differentiation and allow better expansion and maintenance of pluripotency, and/or targeted insertion of a reporter gene in frame with an endogenous gene that is a marker of pluripotency or differentiation state that would allow an easy marker to score differentiation state of stem cells and how changes in media, cytokines, growth conditions, expression of genes, expression of siRNA, shRNA or miRNA molecules, exposure to antibodies to cell surface markers, or drugs alter this state; somatic cell nuclear transfer, for example, a patient's own somatic cells can be isolated, the intended target gene modified in the appropriate manner, cell clones generated (and quality controlled to ensure genome safety), and the nuclei from these cells isolated and transferred into unfertilized eggs to generate patient-specific hES cells that could be directly injected or differentiated before engrafting into the patient, thereby reducing or eliminating tissue rejection; universal stem cells by knocking out MHC receptors (e.g., to generate cells of diminished or altogether abolished immunological identity). Cell types for this procedure include but are not limited to, T-cells, B cells, hematopoietic stem cells, and embryonic stem cells. Additionally, induced pluripotent stem cells (iPSC) may be used which would also be generated from a patient's own somatic cells. Therefore, these stem cells or their derivatives (differentiated cell types or tissues) could be potentially engrafted into any person regardless of their origin or histocompatibility.

The compositions and methods can also be used for somatic cell therapy, thereby allowing production of stocks of cells that have been modified to enhance their biological properties. Such cells can be infused into a variety of patients independent of the donor source of the cells and their histocompatibility to the recipient.

In addition to therapeutic applications, the increased specificity provided by the variants described herein when used in engineered nucleases can be used for crop engineering, cell line engineering and the construction of disease models. The obligate heterodimer cleavage half-domains provide a straightforward means for improving nuclease properties.

The engineered cleavage half domains described can also be used in gene modification protocols requiring simultaneous cleavage at multiple targets either to delete the intervening region or to alter two specific loci at once. Cleavage at two targets would require cellular expression of four ZFNs or TALENs, which could yield potentially ten different active ZFN or TALEN combinations. For such applications, substitution of these novel variants for the wild-type nuclease domain would eliminate the activity of the undesired combinations and reduce chances of off-target cleavage. If cleavage at a certain desired DNA target requires the activity of the nuclease pair A+B, and simultaneous cleavage at a second desired DNA target requires the activity of the nuclease pair X+Y, then use of the mutations described herein can prevent the pairings of A with A, A with X, A with Y and so on. Thus, these FokI mutations decrease non-specific cleavage activity as a result of "illegitimate" pair formation and allow the generation of more efficient orthogonal mutant pairs of nucleases (see U.S. Patent Publication Nos. 2008/0131962 and 2009/0305346).

Also contemplated by the methods and compositions of the invention are the therapeutic treatment of cystic fibrosis. The LNPS may be used to deliver mRNAs encoding the CFTR-specific ZFN, and a donor capable of integrating into the cleaved CFTR gene encoding a fragment of the wildtype CFTR gene such that a functional CFTR protein is expressed. In further embodiments, the LNPs are used to deliver the ZFNs and a corrective oligo is delivered as well which corrects a mutation. In some embodiments, the mutation is the $\Delta 508$ mutation in the CFTR gene.

All patents, patent applications and publications mentioned herein are hereby incorporated by reference in their entireties.

Although disclosure has been provided in some detail by way of illustration and example for the purposes of clarity and understanding, it will be apparent to those of skill in the art that various changes and modifications can be practiced without departing from the spirit or scope of the disclosure. Accordingly, the foregoing disclosure and following examples should not be construed as limiting.

EXAMPLES

Example 1: Preparation of ZFNs

ZFNs targeted to sites in the CFTR gene were designed and incorporated into plasmids vectors essentially as described in Urnov et al. (2005) *Nature* 435(7042): 646-651; Perez et al. (2008) *Nature Biotechnology* 26(7): 808-816; and U.S. Pat. Nos. 9,161,995; 9,394,545; and 9,150,847; International Patent Publication No. WO 2016/183298 and U.S. Patent Publication Nos. 2017/0211075 and 2017/0173080. Linker sequences used between the ZFP DNA binding domain and the nuclease domain were either L0 (LRGSQLVKS, SEQ ID NO:22) or N6a (SGAQSTLDF, SEQ ID NO:23). The ZFNs were tested and all were found to be active. The mouse-CFTR specific ZFNs used are shown below in Table 1, and the sequences that are targeted are shown in Table 2 (see also, International Patent Publication No. WO 2018/204469).

TABLE 1

ZFN designs

| SBS# Domain linker | F1 | F2 | F3 | F4 | F5 | F6 |
|---|---|---|---|---|---|---|
| 56691 L0 | DRSHLTR (SEQ ID NO: 6) | QSGDLTR (SEQ ID NO: 7) | DRSNRTT (SEQ ID NO: 8) | RSDALAR (SEQ ID NO: 9) | RSDNLSE (SEQ ID NO: 10) | ERANRNS (SEQ ID NO: 11) |
| 56690 N6a | DRSALSR (SEQ ID NO: 12) | TSGSLTR (SEQ ID NO: 13) | QSSDLSR (SEQ ID NO: 14) | WRKSLKV (SEQ ID NO: 15) | DRSHLTR (SEQ ID NO: 6) | RLDWLPM (SEQ ID NO: 16) |

TABLE 2

Target sequences

| SBS number | Target sequence (5' -> 3') |
|---|---|
| 56691 | gtCAACAGGTGTACtGCAGGCatgctag (intron 1) (SEQ ID NO: 17) |
| 56690 | ccCTGGGTTATGCTGTGATCttgtgtca (intron 1) (SEQ ID NO: 18) |

ZFNs targeting intron 1 of the murine CFTR gene, shown above in Table 1 was subcloned into individual vectors (pVAV-GEM) containing a T7 RNA polymerase promoter, a 5' UTR containing a sequence derived from the *Xenopus* beta-globin gene, a 3'UTR containing a dual cassette of a sequence derived from the HBB gene, and a 64base pair polyA tract (SEQ ID NO: 26). The sequences of the *Xenopus* 5' UTR, the HBB 3' UTR, and the WPRE 3' UTR were as follows:

```
Xenopus beta-globin 5' UTR (Falcone et at.
(1991) Molecular and Cellular Biology
11(5):2656-2664):
                                    (SEQ ID NO: 19)
5'TGCTTGTTCTTTTTGCAGAAGCTCAGAATAAACGCTCAACTTTGGC

AGATC

Dual HBB 3' UTR (Russell et al. (1996) Blood
87:5314-5323):
                                    (SEQ ID NO: 20)
5'CTAGAAGCTCGCTTTCTTGCTGTCCAATTTCTATTAAAGGTTCCTT

TGTTCCCTAAGTCCAACTACTAAACTGGGGGATATTATGAAGGGCCTT

GAGCATCTGGATTCTGCCTAATAAAAAACATTTATTTTCATTGCTGCG

CTAGAAGCTCGCTTTCTTGCTGTCCAATTTCTATTAAAGGTTCCTTTG

TTCCCTAAGTCCAACTACTAAACTGGGGGATATTATGAAGGGCCTTGA

GCATCTGGATTCTGCCTAATAAAAAACATTTATTTTCATTGCTGCG

WPRE 3' UTR (see U.S. Pat. No. 10,179,918):
                                    (SEQ ID NO: 21)
5'AATCAACCTCTGGATTACAAAATTTGTGAAAGATTGACTGGTATTC

TTAACTATGTTGCTCCTTTTACGCTATGTGGATACGCTGCTTTAATGC

CTTTGTATCATGCTATTGCTTCCCGTATGGCTTTCATTTTCTCCTCCT

TGTATAAATCCTGGTTGCTGTCTCTTTATGAGGAGTTGTGGCCCGTTG

TCAGGCAACGTGGCGTGGTGTGCACTGTGTTTGCTGACGCAACCCCCA

CTGGTTGGGGCATTGCCACCACCTGTCAGCTCCTTTCCGGGACTTTCG

CTTTCCCCCTCCCTATTGCCACGGCGGAACTCATCGCCGCCTGCCTTG

CCCGCTGCTGGACAGGGGCTCGGCTGTTGGGCACTGACAATTCCGTGG

TGTTGTCGGGGAAGCTGACGTCCTTTCCATGGCTGCTCGCCTGTGTTG

CCACCTGGATTCTGCGCGGGACGTCCTTCTGCTACGTCCCTTCGGCCC

TCAATCCAGCGGACCTTCCTTCCCGCGGCCTGCTGCCGGCTCTGCGGC

CTCTTCCGCGTCTTCGCCTTCGCCCTCAGACGAGTCGGATCTCCCTTT

GGGCCGCCTCCCCGCCTG.
```

Example 2: In Vivo Activity mRNA Synthesis:

Messenger RNA (mRNA) was produced of the SpeI-linearized ZFN constructs using in vitro transcription (IVT) at Trilink Biotechnologies with either unmodified residues. mRNA was capped enzymatically post-IVT using the Vaccinia virus capping enzyme along with the mRNA Cap 2'-O-Methyltransferase enzyme to produce "Cap1" mRNA. The mRNA was purified through a silica bead column (for example see Bowman et al. (2012) *Methods* v. 941 Conn G. L. (ed), New York, N.Y. Humana Press), and then packaged (silica-purified).

LNPs:

LNPs were prepared according to the general procedures described in U.S. Patent Publication No. 2019/0060482, incorporated by reference in its entirety as though fully set forth herein.

In Vivo Transduction:

8-10 week old C57BL6 purchased from Charles River were injected intravenously through the tail vein with 200 uL of an aqueous solution containing diluted LNPs. Animals were then sacrificed 14 days post LNP dosing and livers (snap frozen) and lungs (dissociated into single cell suspension via enzymatic digestion) were harvested. Liver gDNA was extracted using a FastPrep-24 Homogenizer (MP Biomedicals), Lysis Matrix D solution (MP Biomedicals), and a MasterPure DNA Purification kit (Epicentre).

Dissociated lung cells were washed, then ran through a column of magnetic beads conjugated to mouse CD45 antibodies (Miltenyi). The CD45+"lung immune" cell fraction was collected and snap frozen prior to gDNA purification (Tissue XS, Macherey Nagel). The CD45− cell flow-through was then split into 2 equal volumetric fractions, which were placed through a column of magnetic beads conjugated to mouse CD326 antibodies or CD31 antibodies to yield epithelial cell or endothelial cell fractions, respectively. These positively selected cell fractions were then individually collected and snap frozen prior to gDNA purification (Tissue XS, Macherey Nagel).

Animals (mice and non-human primates) are also injected with a mixture of diluted LNPs and AAV donor encoding a mouse or human CFTR fragment transgene or CFTR-specific oligonucleotide capable of correcting a CFTR mutation. The transgene contains homology arms flanking the ZFN cut site and a splice acceptor just upstream of the coding sequence of the transgene. The animals are also sacrificed 14 days post LNP dosing and the tissues and cells are isolated as described above. Following the organ harvest, gDNA is isolated as described above.

Indel Analysis (Nuclease Activity):

Primers were designed to amplify approximately 200 bp of total genomic DNA sequence containing the ZFN cut site. Amplicons were then analyzed on either a Miseq or Nextseq (Illumina) and insertions and deletions (indels) from the genomic sequences obtained from the fractionated lung cells and liver cells were quantified.

CFTR Activity Assay:

At animal sacrifice, epithelial cells are isolated and assayed for the amount of CFTR produced and is found in the normal range. In particular, targeted integration of a corrective human CFTR cDNA donor leads to functional correction of CFTR chloride channel electrophysiological activity as assessed by Ussing Chamber measurement. See, e.g., Li et al. (2004) *J. Cystic Fibrosis* 3(Suppl. 2):123-126. Briefly, this assay measures electrical potential difference corresponding to net ion transport across a basal epithelial cell layer. The readout is short-circuit current (Isc) in microamperes over time in minutes. The addition of amiloride inhibits sodium ion conductance, whereas subsequently adding forskolin increases chloride ion conductance. Subsequently adding CFTRinh-172, a commercially available small molecule inhibitor of CFTR chloride channel function, lowers the overall conductance indicating chloride ion transport is specific to the CFTR ion channel. Finally, the addition of uridine 5'-triphosphate (UTP), which stimulates chloride secretion by the basal epithelial cells, increases the current in the Ussing chamber in only the ZFN+ Donor samples and none of the Donor only or ZFN only samples. Use of this assay demonstrates that the insertion of a corrective oligonucleotide or gene fragment via ZFN-directed cleavage restores CFTR function.

Figure 1C:
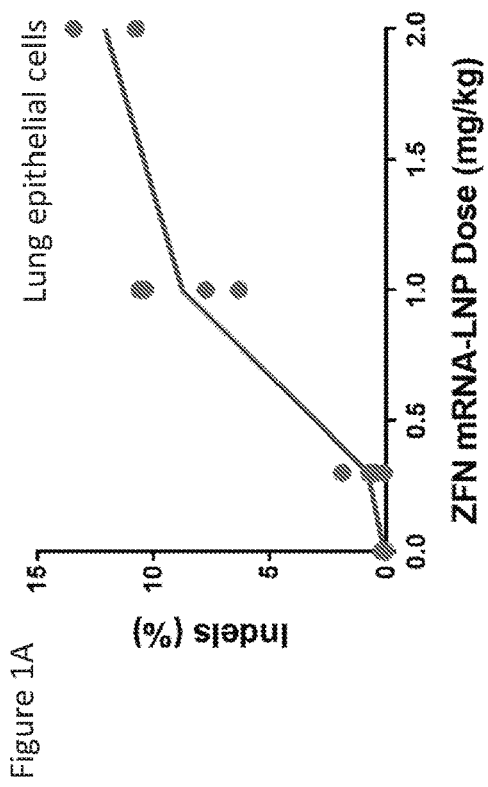
Figure 1B:
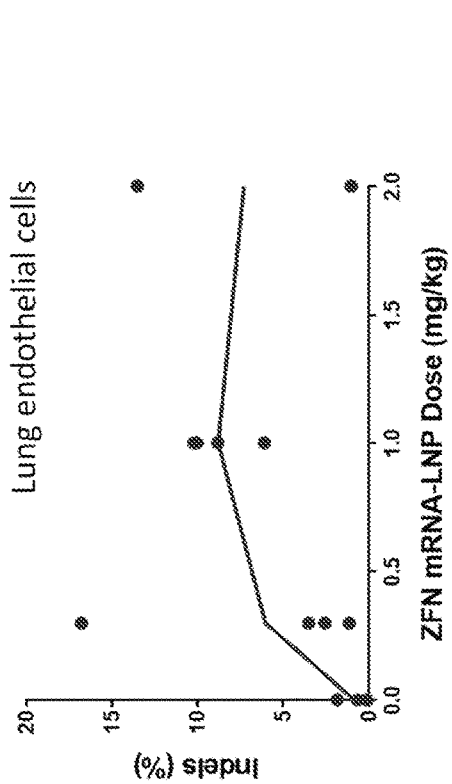
Figure 1D:
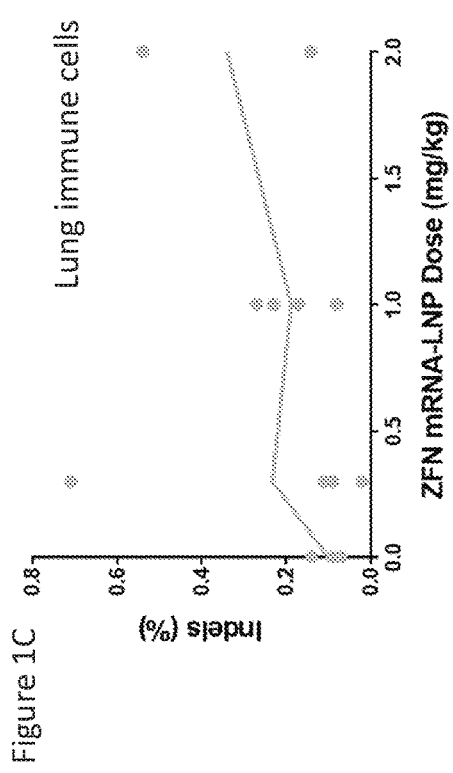
Figure 1E:
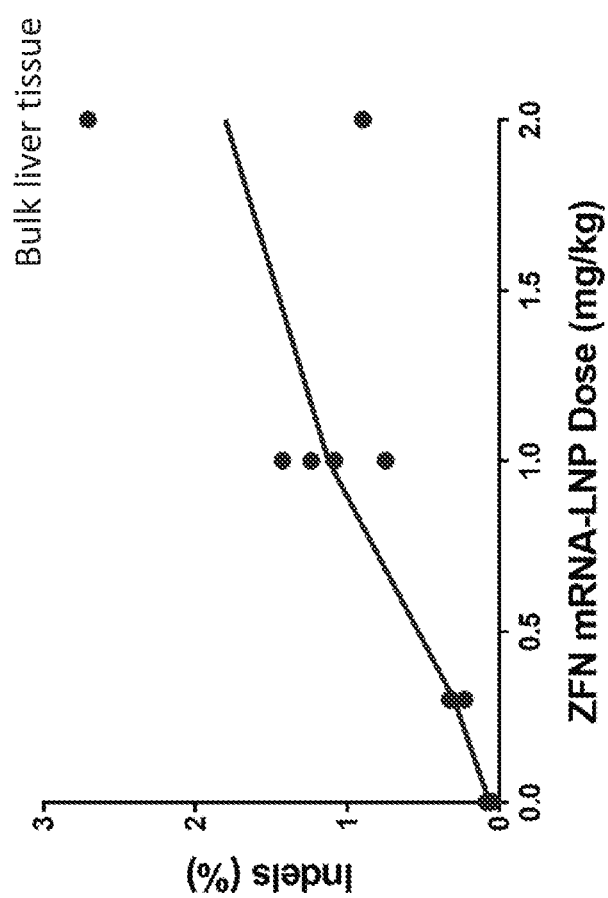

The data (FIG. 1) demonstrated that the ZFNs, delivered by LNP, were capable of cleaving CFTR in vivo in both lung epithelium and lung endothelium (>10% and >7%, respectively), while cleaving CFTR in the liver at >1%. Thus, LNPs allow delivery of ZFNs to pulmonary tissue in live subjects.

What is claimed is:

1. A cationic lipid nanoparticle (LNP) comprising one or more polynucleotides encoding one or more zinc finger protein (ZFP) transcription factors (ZFP-TFs) or one or more zinc finger nucleases (ZFNs), wherein the ZFP-TFs or ZFNs comprise a ZFP designated 56691 or 56690, wherein (i) the ZFP designated 56691 comprises 6 zinc finger domains ordered F1 to F6, the zinc finger domains comprising the following recognition helix regions:
   F1: DRSHLTR (SEQ ID NO: 6);
   F2: QSGDLTR (SEQ ID NO: 7);
   F3: DRSNRTT (SEQ ID NO: 8);
   F4: RSDALAR (SEQ ID NO: 9);
   F5: RSDNLSE (SEQ ID NO: 10); and
   F6: ERANRNS (SEQ ID NO: 11); and (ii) the ZFN designated 56690 comprises 6 zinc finger domains ordered F1 to F6, the zinc finger domains comprising the following recognition helix regions:
   F1: DRSALSR (SEQ ID NO: 12);
   F2: TSGSLTR (SEQ ID NO: 13);
   F3: QSSDLSR (SEQ ID NO: 14);
   F4: WRKSLKV (SEQ ID NO: 15);
   F5: DRSHLTR (SEQ ID NO: 6); and
   F6: RLDWLPM (SEQ ID NO: 16).

2. The cationic LNP of claim 1, wherein the one or more polynucleotides encode the one or more ZFNs and wherein the LNP further comprises one or more donor polynucleotides.

3. The cationic LNP of claim 2, wherein the one or more polynucleotides and/or donor polynucleotide comprise mRNA.

4. The cationic LNP of claim 2, wherein the one or more donor polynucleotides comprise an oligonucleotide that corrects a mutation in the endogenous CFTR gene.

5. The cationic LNP of claim 4, wherein the mutation is a Δ508 mutation.

6. An isolated cell comprising one or more cationic LNPs according to claim 5.

7. The cationic LNP of claim 4, wherein the one or more donor polynucleotides comprise a transgene that expresses a functional CFTR protein.

8. An isolated cell comprising one or more cationic LNPs according to claim 7.

9. An isolated cell comprising one or more cationic LNPs according to claim 2.

10. The isolated cell of claim 9, wherein the cell is a lung cell.

11. A composition comprising the cationic LNP of claim 2, wherein the one or more donor polynucleotides comprise an oligonucleotide that corrects a mutation in the endogenous CFTR gene.

12. The composition of claim 11, wherein the mutation is a Δ508 mutation.

13. The composition of claim 11, wherein the one or more donor polynucleotides comprise a transgene that expresses a functional CFTR protein.

14. The composition of claim 11, wherein the one or more donor polynucleotides are carried on a viral vector.

15. The composition of claim 14, wherein the viral vector is an AAV vector.

16. A method of integrating a donor polynucleotide into an endogenous gene, the method comprising the composition of claim 11 to the cell such that the endogenous gene is cleaved by the one or more ZFNs and the donor polynucleotide is integrated into the cleaved endogenous gene.

17. A method of integrating a donor polynucleotide into an endogenous gene in a cell, the method comprising administering the cationic LNP of claim 2 to the cell such that the endogenous gene is cleaved by the one or more ZFNs and the donor polynucleotide is integrated into the cleaved endogenous gene.

18. The cationic LNP of claim 1 comprising:
   (i) a first cationic lipid at a compositional molar ratio from about 0.18 to about 0.32 and of formula:

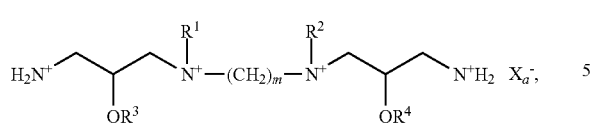

(I)

wherein $R^1$ and $R^2$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ and $R^4$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; m is an integer from 1 to 6; $X_a^-$ is an anion;

(ii) a second cationic lipid at a compositional molar ratio from about 0.24 to about 0.51 and of formula:

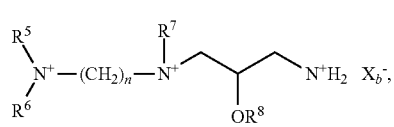

(II)

wherein $R^5$ and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^6$ and $R^7$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; n is an integer from 1 to 6; and $X_b^-$ is an anion;

(iii) a first helper lipid at a compositional molar ratio from about 0.20 to about 0.32;

(iv) a second helper lipid at a compositional molar ratio from about 0.01 to about 0.14; and (v) a biostability enhancing agent at a compositional molar ratio from about 0.01 to about 0.02.

19. An isolated cell comprising one or more cationic LNPs according to claim 1.

20. A composition comprising the cationic LNP of claim 1.

21. A method of modulating endogenous gene expression in a cell, the method comprising administering the cationic LNP of claim 1 to the cell.

22. A method of treating and/or preventing cystic fibrosis in a subject, the method comprising administering the cationic LNP of claim 1 to the subject.

23. The method of claim 22, wherein the cationic LNP of claim 1 is administered 1, 2, 3 or more times to the subject.

24. A kit comprising the cationic LNP of claim 1.

* * * * *

UNITED STATES PATENT AND TRADEMARK OFFICE
CERTIFICATE OF CORRECTION

PATENT NO. : 11,690,921 B2
APPLICATION NO. : 16/413144
DATED : July 4, 2023
INVENTOR(S) : Anthony Conway et al.

It is certified that error appears in the above-identified patent and that said Letters Patent is hereby corrected as shown below:

In the Claims

At Column 67, Line 59, delete "polynucleotide" and insert --polynucleotides--

At Column 68, Line 54, after "comprising" insert --administering--

Signed and Sealed this
Nineteenth Day of September, 2023

Katherine Kelly Vidal
*Director of the United States Patent and Trademark Office*